United States Patent
Zhang

(10) Patent No.: US 11,938,121 B2
(45) Date of Patent: *Mar. 26, 2024

(54) TREATMENT OF INFECTIONS AND BIOFILM FORMATION USING A CELLULOSE SYNTHASE INHIBITOR

(71) Applicant: Purdue Research Foundation, West Lafayette, IN (US)

(72) Inventor: Chunhua Zhang, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 99 days.

This patent is subject to a terminal disclaimer.

(21) Appl. No.: 17/220,975

(22) Filed: Apr. 2, 2021

(65) Prior Publication Data
US 2021/0322394 A1 Oct. 21, 2021

Related U.S. Application Data

(60) Provisional application No. 63/040,594, filed on Jun. 18, 2020, provisional application No. 63/010,312, filed on Apr. 15, 2020.

(51) Int. Cl.
| | |
|---|---|
| *A01N 47/36* | (2006.01) |
| *A01N 47/30* | (2006.01) |
| *A01N 47/34* | (2006.01) |
| *A61K 31/01* | (2006.01) |
| *A61K 31/381* | (2006.01) |
| *A61K 31/44* | (2006.01) |
| *A61K 45/06* | (2006.01) |
| *A61L 2/00* | (2006.01) |
| *A61L 2/16* | (2006.01) |
| *A61P 3/04* | (2006.01) |
| *A61L 101/40* | (2006.01) |
| *A61L 101/44* | (2006.01) |
| *A61P 31/04* | (2006.01) |

(52) U.S. Cl.
CPC .............. *A61K 31/44* (2013.01); *A01N 47/30* (2013.01); *A01N 47/34* (2013.01); *A01N 47/36* (2013.01); *A61K 31/01* (2013.01); *A61K 31/381* (2013.01); *A61K 45/06* (2013.01); *A61L 2/0082* (2013.01); *A61L 2/16* (2013.01); *A61P 3/04* (2018.01); *A61L 2101/40* (2020.08); *A61L 2101/44* (2020.08); *A61L 2202/24* (2013.01)

(58) Field of Classification Search
CPC ........ A01N 47/30; A01N 47/34; A01N 47/36; A61K 45/06; A61K 31/44; A61K 31/17; A61K 31/381; A61K 31/175; A01P 13/00
See application file for complete search history.

(56) References Cited

U.S. PATENT DOCUMENTS

| | | |
|---|---|---|
| 7,241,878 B1 | 7/2007 | Somerville et al. |
| 11,497,213 B2 * | 11/2022 | Zhang ............... A01N 47/34 |
| 2006/0211576 A1 | 9/2006 | Zagar et al. |
| 2008/0233202 A1 | 9/2008 | Wurms et al. |
| 2009/0144849 A1 | 6/2009 | Lutfiyya |
| 2012/0021065 A1 | 1/2012 | Young et al. |
| 2017/0260540 A1 | 9/2017 | Tresch et al. |
| 2020/0068892 A1 | 3/2020 | Zhang |
| 2020/0196599 A1 | 6/2020 | Zhang |
| 2020/0290959 A1 | 9/2020 | Zhang |

FOREIGN PATENT DOCUMENTS

| | | |
|---|---|---|
| CN | 1125719 A | 7/1996 |
| CN | 107041374 A | 8/2017 |
| WO | 2017049016 A1 | 3/2017 |
| WO | 2019112791 A1 | 6/2019 |

OTHER PUBLICATIONS

Huang et al., "Endosidin20-1 is more potent than endosidin20 in inhibiting plant cellulose biosynthesis and molecular docking analysis of cellulose biosynthesis inhibitors on modeled cellulose synthase structure", 2021, The Plant Journal, 106(6), pp. 1605-1624. (doi: 10.1111/tpj.15258) (Year: 2021).*
Taylor N. et al., Interactions among three distinct CesA proteins essential for cellulose synthesis. Proc. Natl. Acad. Sci. USA, vol. 100, 1450-1455, 2003.
Desprez T, et al., Organization of cellulose synthase complexes involved in primary cell wall synthesis in *Arabidopsis thaliana*. Proc. Natl. Acad. Sci. USA, vol. 104, 15572-15577, 2007.
Kumar M, et al., Plant cellulose synthesis: CESA proteins crossing kingdoms., Phytochemistry, vol. 112, 91-99, 2015.
Paredez A. R. et al., Visualization of Cellulose Synthase Demonstrates Functional Associaton with Microtubules. Science, vol. 312,1491-1495, 2006.
International Search Report and Written Opinion for International Application No. PCT/US2018/061962, issued by ISA/US, Commissioner for Patents, dated Mar. 7, 2019, 12 pgs.
Soltani, N. et al., "Potential Corn Yield Losses from Weeds in North America", Weed Technol, vol. 30, pp. 979-984, doi:10.1614/Wt-D-16-00046.1, 2016.
Swanton, C., et al, "Crop Losses Due to Weeds in Canada", Weed Technol, vol. 7, pp. 537-542, 1993.

(Continued)

*Primary Examiner* — My-Chau T. Tran
(74) *Attorney, Agent, or Firm* — Purdue Research Foundation

(57) ABSTRACT

In one embodiment, the present application relates to methods and materials for weed control of a field of a crop plant using a cellulose biosynthesis inhibitor selected from the group consisting of ES20 and ES20-1 to ES20-9 of FIG. 1A. In another embodiment, the present disclosure relates to a method for treatment or prevention of an infection through inhibition of biofilm formation of microorganisms comprising the step of applying a therapeutic effective amount of a cellulose biosynthesis inhibitor selected from the group consisting of ES20 and ES20-1~ES20-9 of FIG. 1A, or a salt thereof, in combination with one or more other commonly used antibiotics. A composition matter comprising said compounds and methods of use are within the scope of the present invention.

5 Claims, 14 Drawing Sheets
(14 of 14 Drawing Sheet(s) Filed in Color)

(56) References Cited

OTHER PUBLICATIONS

Soltani, N. et al. "Potential Yield Loss in Dry Bean Crops Due to Weeds in the United States and Canada", Weed Technol, vol. 32, pp. 342-346, doi:10.1017/wet.2017.116, 2018.
Gianessi, L. P. "The increasing importance of herbicides in worldwide crop production", Pest Manag Sci, vol. 69, pp. 1099-1105, doi:10.1002/ps.3598, 2013.
Funke, T., et al., "Molecular basis for the herbicide resistance of Roundup Ready crops", Proc Natl Acad Sci U S A, vol. 103, pp. 13010-13015, doi:10.1073/pnas.0603638103, 2006.
Edwards, C. B. et al. "Benchmark study on glyphosate-resistant crop systems in the United States. Economics of herbicide resistance management practices in a 5 year field-scale study", Pest Manag Sci, vol. 70, pp. 1924-1929, doi:10.1002/ps.3759, 2014.
Beres, Z. T. et al., "High Levels of Glyphosate Resistance in Conyza canadensis from Agricultural and Non-Agricultural Sites in Ohio and Iowa", Sci Rep 8, pp. 8, doi: 10.1038/s41598-018-28163-w, 2018.
Morran, S., et al., "Multiple target site resistance to glyphosate in junglerice (*Echinochloa colona*) lines from California orchards", Pest Manag Sci, vol. 74, pp. 2747-2753; doi: 10.1002/ps.5061, 2018.
Heim, D., et al, "Mutation of a Locus of *Arabidopsis thaliana* Confers Resistance to the Herbicide Isoxaben", Plant Physiol, vol. 90, pp. 146-150, 1989.
Scheible, W., et al., "Modifications of cellulose synthase confer resistance to isoxaben and thiazolidinone herbicides in *Arabidopsis* lxr1 mutants", Proc Natl Acad Sci U S A, vol. 98, pp. 10079-10084, doi:10.1073/pnas.191361598, 2001.
Desprez, T. et al., "Resistance against herbicide isoxaben and cellulose deficiency caused by distinct mutations in same cellulose synthase isoform CESA6", Plant Physiol, vol. 128, pp. 482-490, 2002.
Brabham, C. et al., "Indaziflam herbicidal action: a potent cellulose biosynthesis inhibitor", Plant Physiol, vol. 166, pp. 1177-1185, doi:10.1104/pp. 114.241950, 2014.
Hu, Z. et al., "Genome-Editing Based Engineering of CESA3 Dual Cellulose-Inhibitor Resistant Plants", Plant Physiol, vol. 180, pp. 827-836, doi:10.1104/pp. 18.01486, 2019.
Gallery Infosheet—Gallery Specialty Herbicide, Dow AgroSciences (cached wayback machine Jun. 10, 2016: https://web.archive.org/web/20160610020859/http://newsomseed.com/resources/GalleryBrochure.pdf) no pagination, 2 pages, 2016.
Norsworthy, J. K., et al., Reducing the Risks of Herbicide Resistance: Best Management Practices and Recommendations, Weed Science, 2012, 60(sp1), 31-62, 2012.
Drakakaki, G. et al., "Clusters of bioactive compounds target dynamic endomembrane networks in vivo," Proc. Natl. Acad. Sci., 108(43), 17850-17855, 2011.
Baumann, P.A., Texas Cooperative Extension, The Texas A&M University System, "Suggestions for weed control in corn," http://counties.agrilife.org/colorado/files/2011/08/weed-control-for-corn_20.pdf, 2011, 27 pg.
Huang, L., et al., "Use Endosidin2 to Study Plant Exocytosis and Vacuolar Trafficking", Methods in Mol Biol 1789, Chapter 13, pp. 167-175, 2018.
Zhang, C., et al., "Endosidin2 targets conserved exocyst complex subunit EXO70 to inhibit exocytosis", Proc Natl Acad Sci, pp. E41-E50, 2015.
International Preliminary Report on Patentability for International Application No. PCT/US2018/061962, issued by The International Bureau of WIPO, dated May 26, 2020, 8 pgs.
Arioli, T. et al., Molecular analysis of cellulose biosynthesis in *Arabidopsis*. Science, vol. 279, 717-20, 1998.
Bennion, B. J. et al., Predicting a Drug's Membrane Permeability: A Computational Model Validated With in Vitro Permeability Assay Data. J Phys Chem B, vol. 121, 5228-5237, 2017.
Castiblanco, L. F. et al., Cellulose production, activated by cyclic di-GMP through BcsA and BcsZ, is a virulence factor and an essential determinant of the three-dimensional architectures of biofilms formed by Erwinia amylovora Ea1189. Mol Plant Pathol, 19,vol. 90-103, 2018.
Giddings, T. H. et al., Visualization of particle complexes in the plasma membrane of Micrasterias denticulata associated with the formation of cellulose fibrils in primary and secondary cell walls. J Cell Biol, vol. 84, 327-39, 1980.
Gutierrez, R. et al., *Arabidopsis* cortical microtubules position cellulose synthase delivery to the plasma membrane and interact with cellulose synthase trafficking compartments. Nat Cell Biol, vol. 11, 797-806, 2009.
Hill, J. L. et al., The *Arabidopsis* cellulose synthase complex: a proposed hexamer of CESA trimers in an equimolar stoichiometry. Plant Cell, vol. 26, 4834-42, 2014.
Hu, Z. et al., Mitochondrial Defects Confer Tolerance against Cellulose Deficiency. Plant Cell, vol. 28, 2276-2290, 2016.
Huang, L. et al., Endosidin2-14 targets the exocyst complex in plants and fungal pathogens to inhibit exocytosis. Plant Physiol, vol. 180, 1756-1770, 2019.
Huang, L. et al., Endosidin20 Targets the Cellulose Synthase Catalytic Domain to Inhibit Cellulose Biosynthesis. Plant Cell, vol. 32, 2141-2157, 2020.
Huang, L. et al., Endosidin20 does not affect cellulose synthase complex transport from ER to the Golgi. Plant Signal Behav, vol. 15, 1780039, 2020.
Li, S. et al., Cellulose synthase complexes act in a concerted fashion to synthesize highly aggregated cellulose in secondary cell walls of plants. Proc Natl Acad Sci U S A, vol. 113, 11348-11353, 2016.
Limoli, D. H. et al., Bacterial Extracellular Polysaccharides in Biofilm Formation and Function. Microbiol Spectr, vol. 3, 2016.
Mcnamara, J. T. et al., A molecular description of cellulose biosynthesis. Annu Rev Biochem, vol. 84, 895-921, 2015.
Morgan, J. L. et al., Mechanism of activation of bacterial cellulose synthase by cyclic di-GMP. Nat Struct Mol Biol, vol. 21, 489-96, 2014.
Morgan, J. L. et al., Crystallographic snapshot of cellulose synthesis and membrane translocation. Nature, vol. 493, 181-6, 2013.
Pear, J. R. et al., Higher plants contain homologs of the bacterial celA genes encoding the catalytic subunit of cellulose synthase. Proc Natl Acad Sci U S A, vol. 93, 12637-42, 1996.
Purushotham, P. et al., Architecture of a catalytically active homotrimeric plant cellulose synthase complex. Science, vol. 369, 1089-1094, 2020.
Ross, P. et al., Cellulose biosynthesis and function in bacteria. Microbiol Rev, vol. 55, 35-58, 1991.
Shim, I. et al., Alleles Causing Resistance to Isoxaben and Flupoxam Highlight the Significance of Transmembrane Domains for CESA Protein Function. Front Plant Sci, vol. 9, 1152, 2018.
Strap, J. L. et al., Characterization of pellicle inhibition in Gluconacetobacter xylinus 53582 by a small molecule, bellicin, identified by a chemical genetics screen. PLOS One, 6(12), e28015, 2011.
Trott, O. et al., AutoDock Vina: improving the speed and accuracy of docking with a new scoring function, efficient optimization, and multithreading. J Comput Chem, vol. 31, 455-61, 2010.
Waterhouse, A. et al., Swiss-Model: homology modelling of protein structures and complexes. Nucleic Acids Res, vol. 46, W296-W303, 2018.
Xu, J. et al., Dissection of *Arabidopsis* ADP-Ribosylation Factor 1 function in epidermal cell polarity. Plant Cell, vol. 17, 525-36, 2005.
Zhang, W. et al., Myosins XI Are Involved in Exocytosis of Cellulose Synthase Complexes. Plant Physiol, vol. 179, 1537-1555, 2019.
Zhang, Y. et al., Golgi-localized STELLO proteins regulate the assembly and trafficking of cellulose synthase complexes in *Arabidopsis*. Nat Commun, vol. 7, 11656, 2016.

\* cited by examiner

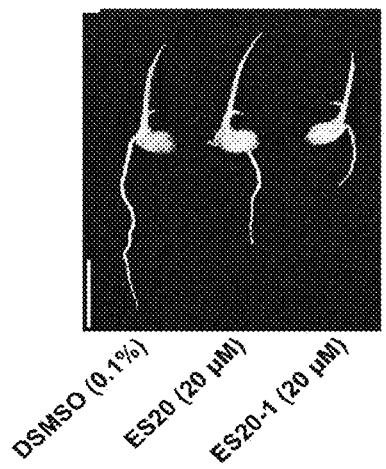
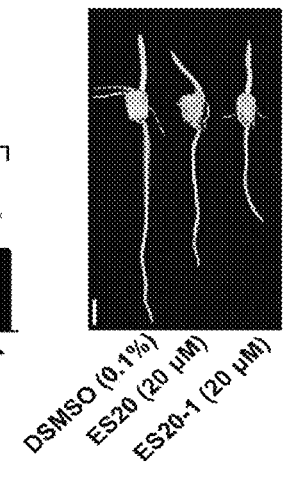
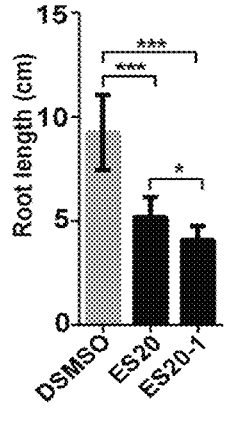
FIG. 3D     FIG. 3E     FIG. 3F     FIG. 3G

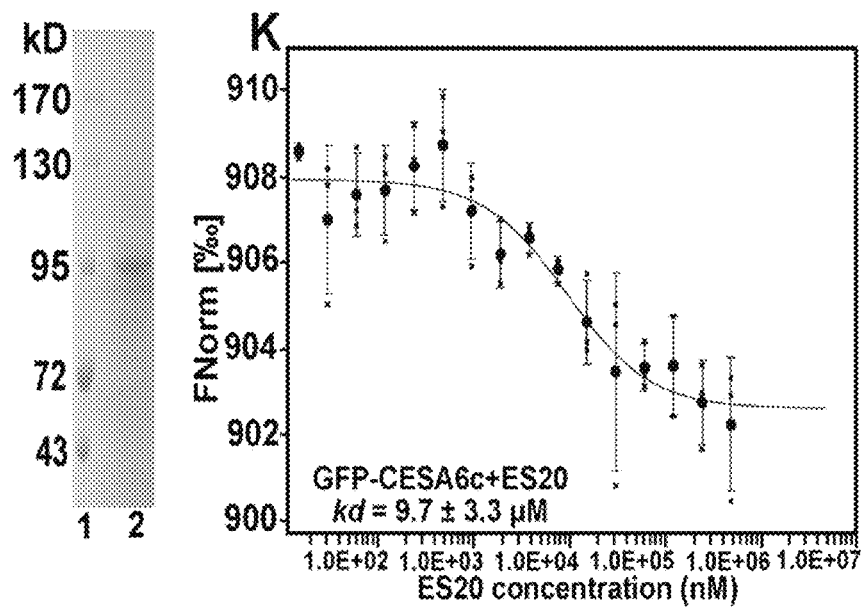
FIG. 3J
FIG. 3K
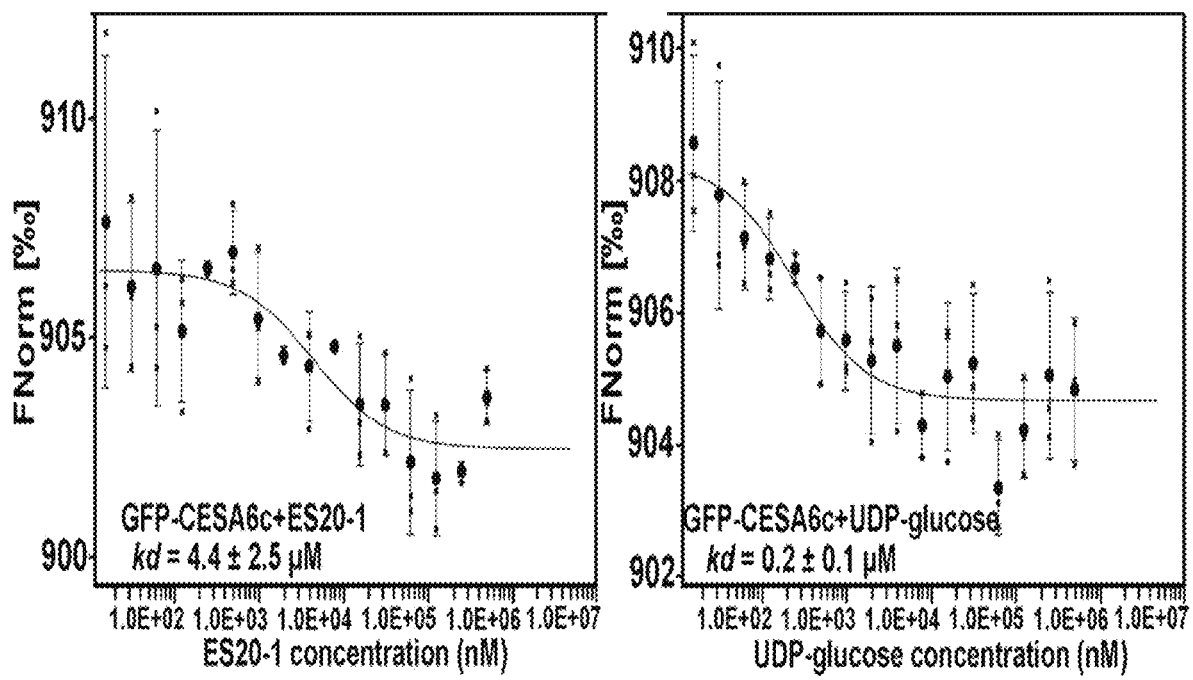
FIG. 3L
FIG. 3M

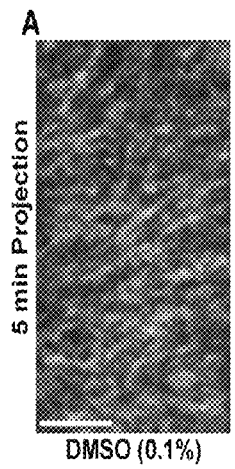
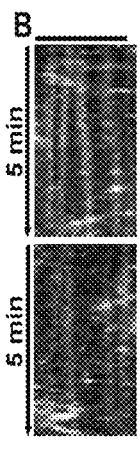
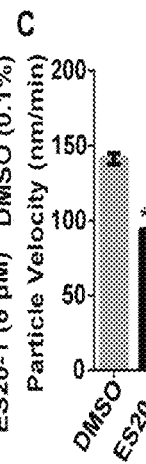
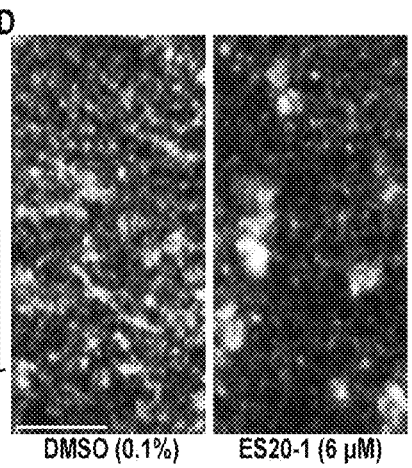
FIG. 4A     FIG. 4B    FIG. 4C     FIG. 4D
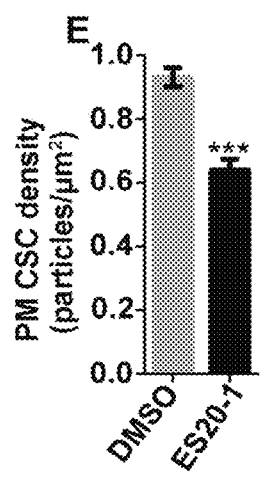
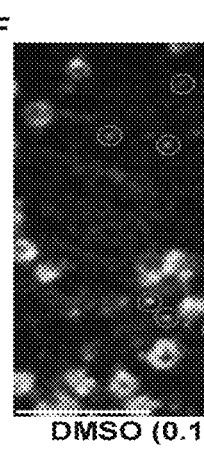
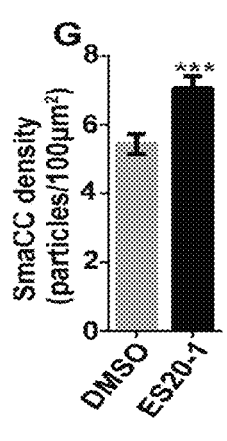
FIG. 4E          FIG. 4F          FIG. 4G

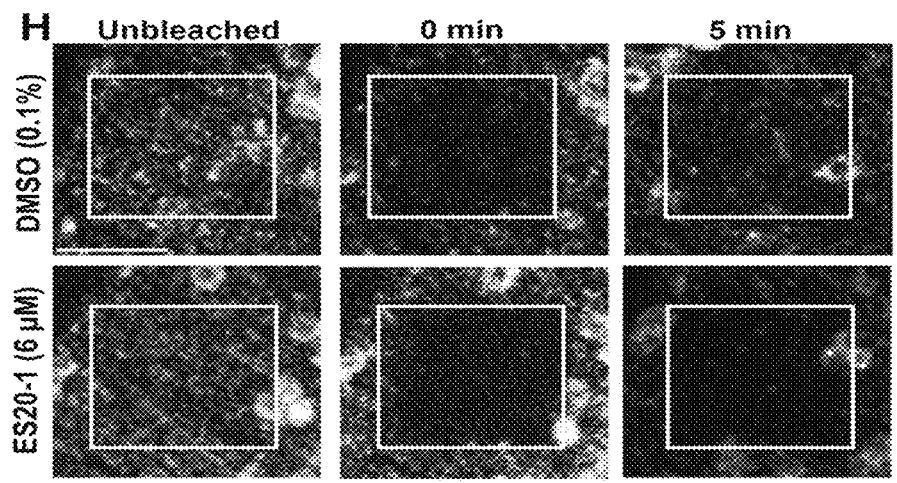
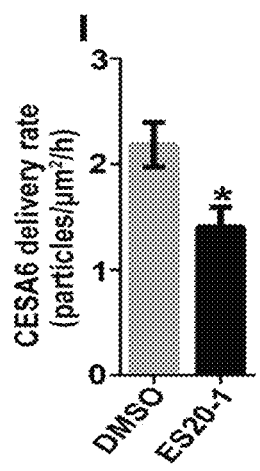
FIG. 4H
FIG. 4I
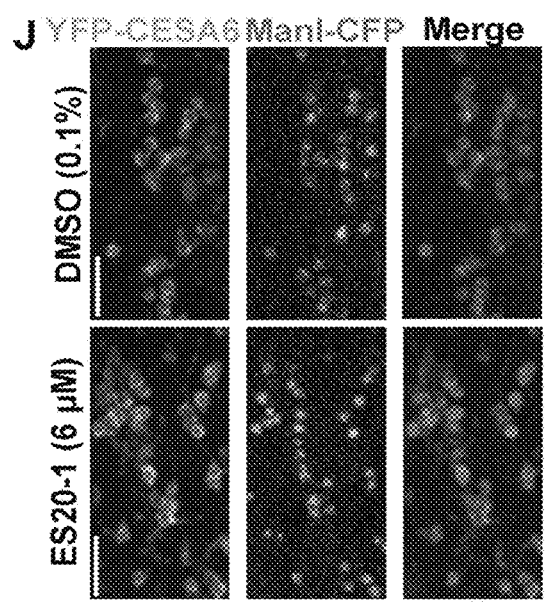
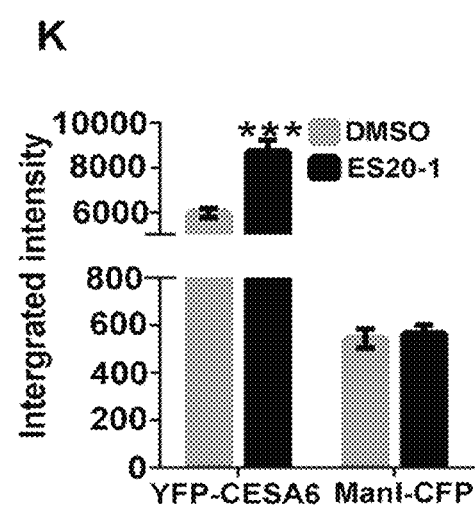
FIG. 4J
FIG. 4K

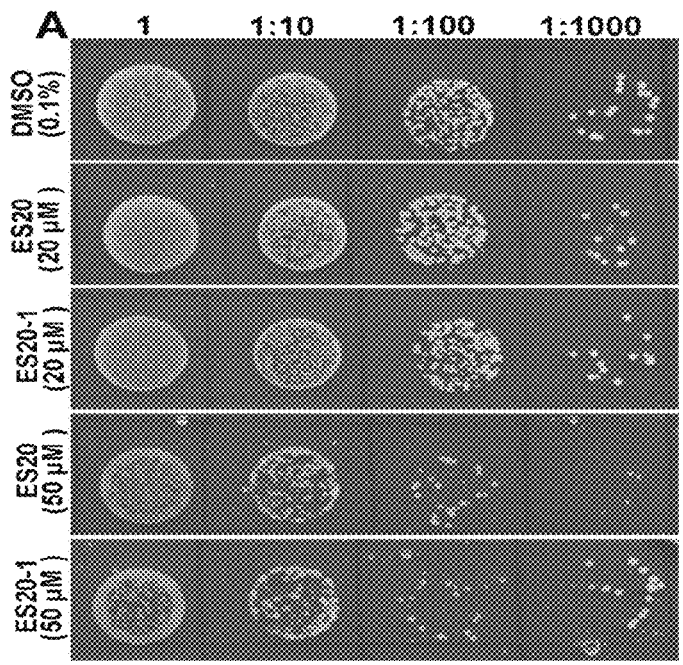
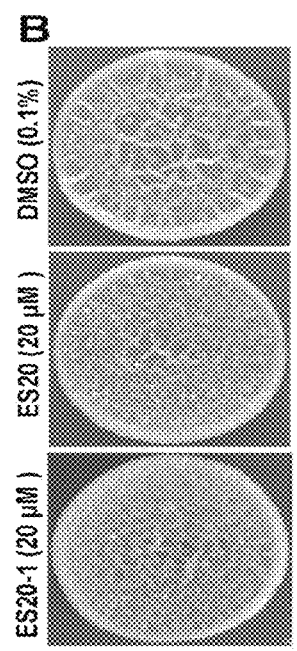
FIG. 6A
FIG. 6B
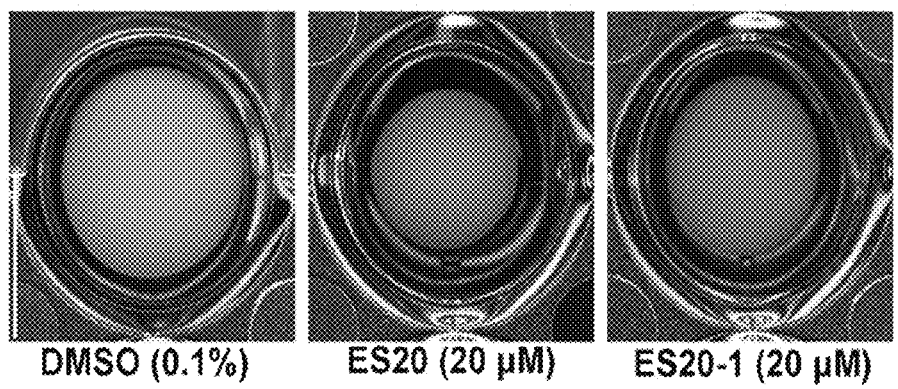
FIG. 6C
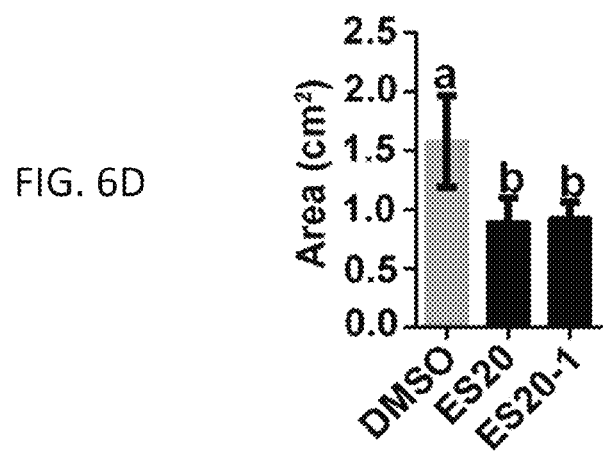
FIG. 6D

TREATMENT OF INFECTIONS AND BIOFILM FORMATION USING A CELLULOSE SYNTHASE INHIBITOR

CROSS-REFERENCE TO RELATED APPLICATIONS

The present U.S. patent application is related to and claims the priority benefit of U.S. Provisional Patent Application Ser. No. 63/010,312, filed Apr. 15, 2020, and U.S. Provisional Patent Application Ser. No. 63/040,594, filed Jun. 18, 2020, the contents of which are hereby incorporated by reference in their entirety into the present disclosure.

STATEMENT OF GOVERNMENT SUPPORT CLAUSE

This invention was made with government support under MCB2025437 awarded by the National Science Foundation. The government has certain rights in the invention.

TECHNICAL FIELD

The present application relates to methods and materials useful for the treatment of infections and biofilm formation by a cellulose synthase inhibitor. A composition matter comprising said compounds and methods of use are within the scope of the present invention.

BACKGROUNDS AND SUMMARY OF THE INVENTION

This section introduces aspects that may help facilitate a better understanding of the disclosure. Accordingly, these statements are to be read in this light and are not to be understood as admissions about what is or is not prior art.

Cellulose is the polymer of β-(1,4) D-glucose that serves as an important component of plant cell to control plant cell morphogenesis and growth. Some bacteria also produce cellulose and secrete it out of cells to form the extracellular matrix named biofilm (Ziemba, C et al, *NPJ Biofilms Microbiomes,* 2016, 2, 1; Limoli, D H, et al., *Microbiol Spectr.* 2015, 3; Mann, E E, et al, *FEMS Microbiol Rev.* 2012, 36, 893-916). Cellulose from plant biomass and from bacterial fermentation serves as critical resource to meet tremendous fiber supply requirement. However, biofilms also cause human and animal tooth decay and many other types of infectious diseases such as urinary tract infection, cystic fibrosis and middle-ear infections (Bjarnsholt, T. *APMIS Suppl.* 2013, 1-51). The extracellular matrix of biofilms protects the bacterium from biotic and abiotic stresses and made the bacterium in biofilms difficult to manipulate. The application of general antibiotics often fails to cure biofilm infections and there is great need to develop alternative methods to control biofilms[5].

Inhibition of cellulose biosynthesis has the potential to inhibit the formation of biofilms extracellular matrix and makes it possible to overcome biofilm antibiotic resistance and control corresponding diseases caused by biofilms more efficiently. The cellulose biosynthesis inhibitor Endosidin20 and its analogues disclosed herein target the conserved catalytic site of plant cellulose synthase. Because the amino acids at the key motifs of the catalytic sites are highly conserved between plant and bacterial cellulose synthase, we believe our novel plant cellulose synthase inhibitor will target bacterial cellulose synthase as well to inhibit cellulose biosynthesis and biofilm formation. We performed molecular docking analysis and found that Endosidin20 can target the catalytic site of bacterial cellulose synthase as well. We tested the effect of Endosidin20 in the growth of cellulose-producing bacteria *Rhodobacter sphaeroidesin* and found that Endosidin20 can indeed inhibit the growth of *Rhodobacter sphaeroidesin*. Our data indicate that Endosidin20 not only affects plant cellulose synthesis, but also significantly inhibits bacterial cellulose biosynthesis as well.

Cellulose, the main component of the plant cell wall, provides a stable environment for cells and is the most abundant source of biomass on Earth. Endosidin20 (ES20) is a recently identified cellulose biosynthesis inhibitor that targets the catalytic site of plant cellulose synthase (CESA). Here, we screened over 600 Endosidin20 and its analogs for their inhibitory effects on plant growth and identified nine active analogs named ES20-1 to ES20-9. Among these, ES20-1 had stronger inhibitory effects on plant growth and cellulose biosynthesis than ES20. Previously identified *Arabidopsis thaliana* cesa6 alleles that reduce plant sensitivity to ES20 also caused reduced sensitivity to ES20-1 and other active analogs except ES20-6 and ES20-8 in terms of plant growth. At the biochemical level, ES20-1 directly interacts with *Arabidopsis thaliana* CESA6 (AtCESA6). At the cellular level, this molecule, like ES20, induced the accumulation of cellulose synthase complexes (CSCs) at the Golgi apparatus and inhibited their secretion to the plasma membrane. Like ES20, ES20-1 likely targets the catalytic site of CESA.

Other common cellulose producing bacteria are *G. xylinus, Agrobacterium tumefaciens, Rhizobium leguminosarum* bv. trifohi, *Sarcina ventriculi, Salmonella* spp., *Escherichia coli, Klebsiella pneumoniae*, cyanobacteria and Gram-positive bacterium *S. ventriculi* (Ross, P., et al., *Microbiol Rev* 55, 35-58 (1991); Romling, U. *Res Microbiol* 153, 205-212 (2002)).

We have discovered that Endosidin20 and its active analogs are novel group of bacterial cellulose biosynthesis inhibitor that can be used to control bacterial growth and biofilm formation and may offer a unique alternative option in fighting various bacterial and fungal infections. The invention disclosed herein may find potential applications in agricultural industry as well as therapeutic uses for diseases caused by fungal and bacterial infections.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 1A. Chemical structures of the nine active ES20 analogs. FIG. 1B. Representative 5-day-old *Arabidopsis* Col-0 seedlings grown on medium supplemented with different concentrations of ES20 and ES20 active analogs. Scale bar: 1 cm. FIG. 1C. Quantification of root length in 5-day-old Col-0 seedlings described in B. Data represent mean±SD (n=12 seedlings). FIG. 1D and FIG. 1E. Nine ES20 active analogs induce root swelling. FIG. 1D. Representative images of the roots of 5-day-old *Arabidopsis* Col-0 seedlings grown on standard growth medium and incubated overnight in growth medium supplemented with 0.1% DMSO or 6 μM ES20 analogs. Scale bar: 0.5 cm. FIG. 1E. Quantification of root width in the elongation zone in the seedlings described in FIG. 1D. Data represent mean±SD (n=12 seedlings). FIG. 1F. Representative phloroglucinol stained root images of 5-day-old *Arabidopsis* Col-0 seedlings grown on growth medium supplemented with 0.1% DMSO or different concentrations of ES20 analogs. All active ES20 analogs cause ectopic lignin accumulation. FIG. 1G. Quantification of root cell wall crystalline cellulose content of 7-day-old light-grown Col-0 seedlings grown on growth medium supplemented with 0.1% DMSO or different concentrations of active ES20 analogs. Data represent mean±SD (n=3 biological replicates). All nine active ES20 analogs cause crystalline cellulose content reduction of cell wall. Statistically significant differences in FIG. 1C and FIG. 1E were determined using one-way ANOVA followed by Tukey's multiple comparisons test. Different letters indicate significant differences between groups (p<0.05). In FIG. 1G, *** indicates p<0.001 by one-way ANOVA followed by Dunnett's test compared with DMSO.

FIG. 2A. Representative 6-day-old seedlings of EMS-induced mutants with reduced sensitivity to ES20 grown on growth medium supplemented with DMSO (0.1%) or different concentrations of ES20 analogs. Scale bars: 1 cm. FIG. 2B. Representative 6-day-old transgenic plants expressing AtCESA6 carrying missense mutations in prc1-1 grown on growth medium supplemented with DMSO (0.1%) or different concentrations of ES20 analogs. Scale bars: 1 cm.

FIG. 3A to FIG. 3G. ES20-1 is more potent than ES20 in inhibiting plant growth and cellulose synthesis. FIG. 3A. Representative 5-day-old dark-grown *Arabidopsis* Col-0 seedlings grown on growth medium supplemented with different concentrations of ES20 or ES20-1. Scale bar: 1 cm. FIG. 3B. Quantification of hypocotyl length of 5-day-old dark-grown *Arabidopsis* Col-0 seedlings described in FIG. 3A. Data represent mean±SD (n=12 seedlings). FIG. 3C. Quantification of crystalline cellulose content in the hypocotyl cell walls of 7-day-old dark-grown Col-0 seedlings grown on growth medium supplemented with DMSO (0.1%), 1 µM ES20, or 1 µM ES20-1. Data represent mean±SD (n=3 biological replicates). FIG. 3D and FIG. 3E. ES20-1 is more potent than ES20 in inhibiting rice root growth. FIG. 3D. Representative image of 6-day-old rice seedlings grown in sterile water supplemented with DMSO (0.1%), 20 µM ES20, or 20 µM ES20-1. Scale bar: 1 cm. FIG. 3E. Quantification of root length of rice seedlings as described in FIG. 3D. Data represent mean±SD (n=10 seedlings). FIG. 3F and FIG. 3G. ES20-1 is more potent than ES20 in inhibiting maize root growth. FIG. 3F. Representative image of 6-day-old maize seedlings grown in sterile water supplemented with DMSO (0.1%), 20 µM ES20, or 20 µM ES20-1. Scale bar: 1 cm. FIG. 3G. Quantification of root length of maize seedlings as described in FIG. 3F. Data represent mean±SD (n=12 seedlings). FIG. 3H. Representative immunoblot from a DARTS assay of ES20-1 and YFP-AtCESA6. FIGS. 3J-3N. CESA6c interacts with ES20-1 and UDP-glucose in an MST assay. FIG. 3J. Coomassie blue staining of purified GFP-tagged CESA6c with a His-SUMO tag (lane 2). FIGS. 3K, 3L, 3M, 3N. Thermophoresis binding curves showing a direct interaction between GFP-CESA6c and ES20 (FIG. 3K), ES20-1 (FIG. 3L), UDP-glucose (FIG. 3M), ES20-9 (FIG. 3N), respectively. FIGS. 3O-3Q, ES20 and ES20-1 interact with GFP-CESA6c$^{P595S}$ in an MST assay. FIG. 3O. Coomassie blue staining of purified GFP-tagged CESA6c$^{P595S}$ with a His-SUMO tag (lane 2). FIG. 3P and FIG. 3Q. Thermophoresis binding curves showing a direct interaction between GFP-CESA6c$^{P595S}$ and ES20 (FIG. 3P) and ES20-1 (FIG. 3Q). Statistically significant differences in FIG. 3B were determined using one-way ANOVA followed by Tukey's multiple comparisons test. Lower-case letters represent ANOVA results for plants grown on medium with 0.1% DMSO, different concentrations of ES20 or ES20-1. Different letters indicate significant differences between groups (p<0.05). In FIGS. 3C, 3E, 3G, and 3I, * indicates p<0.05,  indicates p<0.01, and * indicates p<0.001 by two-tailed Student's t test.

FIGS. 4A-4K. ES20-1 disrupts the trafficking of CSCs to the PM. FIG. 4A to FIG. 4C. ES20-1 reduces the motility of CSCs at the PM. FIG. 4A. Representative time projections using average intensity images from a time-lapse series of YFP-AtCESA6 particles in root epidermal cells treated with 0.1% DMSO or 6 µM ES20-1 for 30 min. FIG. 4B. Representative kymographs of the trajectories of YFP-AtCESA6 particles from 0.1% DMSO- or 6 µM ES20-1-treated seedlings as described in FIG. 4A. FIG. 4C, Quantification of YFP-AtCESA6 particle velocity after 30 min treatment with 0.1% DMSO or 6 µM ES20-1. Data represent mean±SE (n=325 CSC trajectories from 6 seedlings per treatment). FIG. 4D and FIG. 4E. ES20-1 treatment reduces the abundance of PM-localized YFP-AtCESA6 in root epidermal cells. FIG. 4D. Representative images of PM-localized YFP-AtCESA6 in root epidermal cells treated with 0.1% DMSO or 6 µM ES20-1 for 10 min. FIG. 4E. Quantification of CSC density at the PM in YFP-AtCESA6 seedlings treated with 0.1% DMSO or 6 µM ES20-1 as described in FIG. 4D. Data represent mean±SE (n=32 cells from 16 seedlings). FIG. 4F and FIG. 4G. 10 min ES20-1 treatment increases the density of cortical SmaCCs, as indicated by red circles. Data in G represent mean±SE (n=24 cells from 12 seedlings per treatment). FIG. 4H and FIG. 4I. ES20-1 treatment reduce the delivery rate of CSCs to the PM in root epidermal cells. FIG. 4H. Representative images of CSCs at PM during FRAP analysis. FIG. 4I. Quantification of delivery rate of CSCs based on FRAP assay as mentioned in FIG. 4H. Data represent mean±SE (n=10 cells from 10 seedlings per treatment). FIG. 4J and FIG. 4K. ES20-1 increases the abundance of CSC at the Golgi. FIG. 4J. Representative images of Golgi-localized YFP-AtCESA6 and ManI-CFP after 0.1% DMSO or 6 µM ES20-1 treatment for 1 h. FIG. 4K. Quantification of integrated fluorescence intensity of Golgi-localized CSCs and ManI as described in FIG. 4J. Data represent mean±SE (n=55 from 11 seedlings). Scale bars: 5 µm. In FIGS. 4C, 4E, 4G, 4I, and 4K, * indicates p<0.05 and *** indicates p<0.001 by two-tailed Student's t test.

FIG. 5A. The predicted binding site for ES20-1 and ES20 on modeled full-length AtCESA6 structure with the highest binding affinity. Green: elongating glucan chain. Red sticks: the amino acids that are required for the inhibitory effect of ES20 identified through EMS mutant screening. Yellow: ES20. Magenta: ES20-1. The amino acids in conserved TED, DCD, DDG, and QVLRW motifs are highlighted as spheres. The IF2, IF3, CSR and PCR are highlighted by corresponding colors marked on the figure. FIG. 5B. The predicted binding site as shown in FIG. 5A without highlighting TED, DCD, DDG, and QVLRW motifs. Blue sticks:

the amino acids in the catalytic site that are required for the inhibitory effect of ES20 identified through predictions based on previous molecular docking analysis using modeled structure of CESA6 central cytoplasmic domain. FIG. 5C and FIG. 5D. Focused top (FIG. 5C) and side (FIG. 5D) views of the predicted binding site for ES20 (yellow) and ES20-1 (magenta) as shown in FIG. 5B.

FIGS. 6A-6D. ES20 and ES20-1 inhibit bacterial cell growth and cellulose biosynthesis. FIGS. 6A and 6B. ES20 and ES20-1 inhibits the cell growth and colony morphology of *K. xylinus*. FIG. 6A. Representative images of series diluted *K. xylinus* cells grown on HS solid medium supplemented with DMSO (0.1%) and different concentrations of ES20 and ES20-1 for 6 days. FIG. 6B. The morphology of *K. xylinus* colonies grown on HS solid medium supplemented with DMSO (0.1%), 20 µM ES20 or 20 µM ES20-1 for 6 days. FIGS. 6C and 6D. ES20 and ES20-1 inhibit cellulose production in *K. xylinus* under agitated culture conditions. FIG. 6C. Representative images of *K. xylinus* cultures in growth medium supplemented with 0.1% DMSO, 20 µM ES20, or 20 µM ES20-1 after 5 days of agitated cultivation. Scale bar: 1 cm. The white ball-shaped structures represent cellulose clusters. FIG. 6D. Quantification of the sizes of cellulose clusters in cultures containing 0.1% DMSO, 20 µM ES20, or 20 µM ES20-1 as described in FIG. 6C. Data represent mean±SD (n=3 biological replicates).

DETAILED DESCRIPTION

Figure 1A:
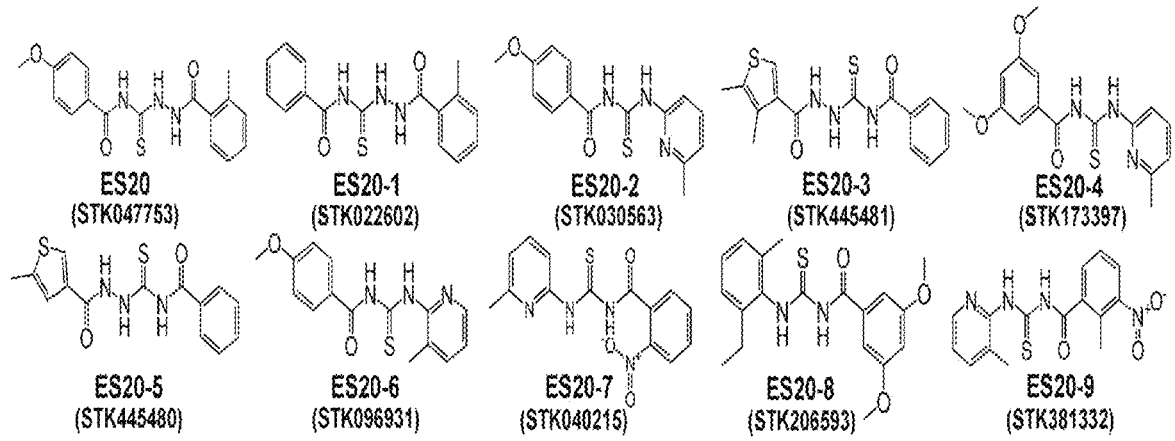
FIGS. 1A-1G. ES20 analogs inhibit plant cellulose synthesis.
Figure 1B:
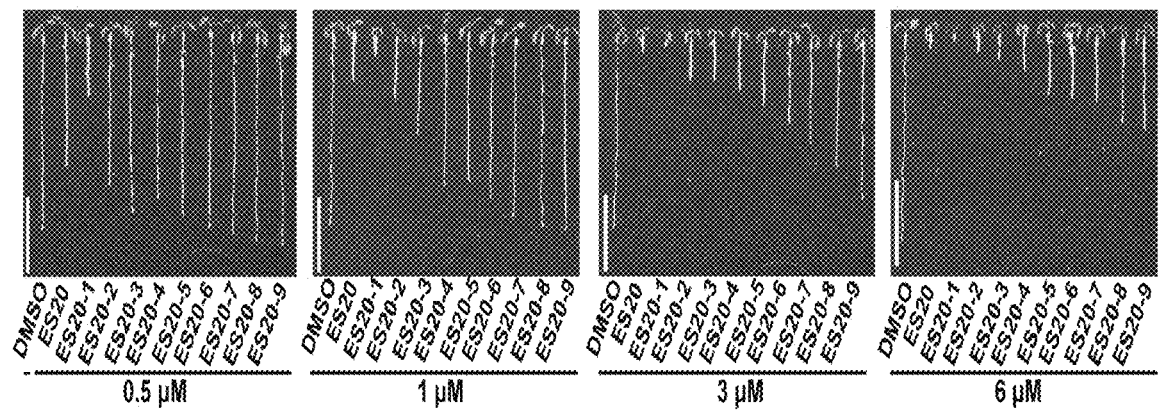
Figure 1C:
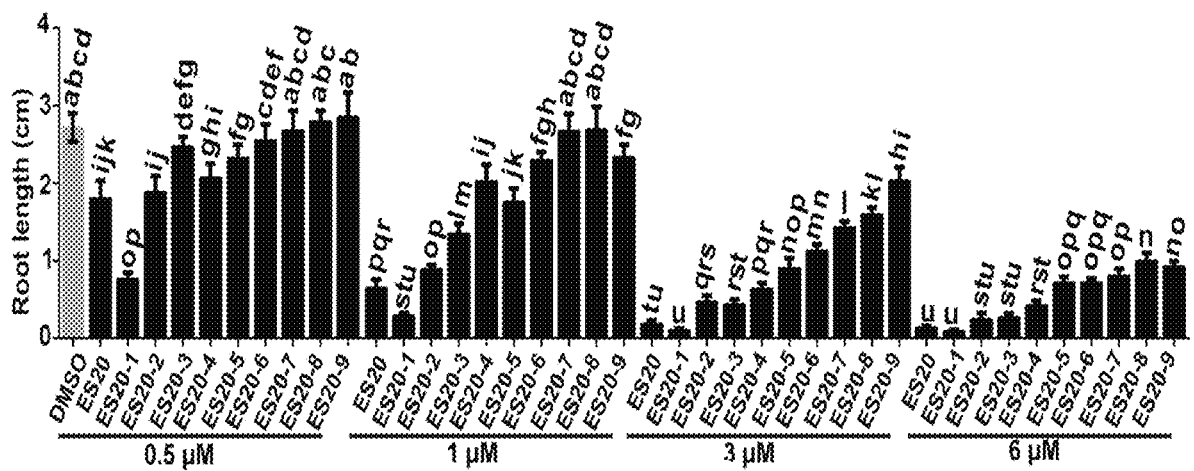

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure, the term "about" can allow for a degree of variability in a value or range, for example, within 20%, within 10%, within 5%, or within 1% of a stated value or of a stated limit of a range.

In the present disclosure, the term "substantially" can allow for a degree of variability in a value or range, for example, within 70%, within 80%, within 90%, within 95%, or within 99% of a stated value or of a stated limit of a range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

Our previous patent applications Zhang, et al., Ser. No. 16/559,799, filed Sep. 4, 2019, entitled "SYNERGISTIC EFFECT OF ISOXABEN AND CELLULOSIN AS A HERBICIDE", Zhang, et al., PCT/US18/61962, filed Nov. 20, 2018, entitled "CELLULOSE SYNTHASE INHIBITORS AS A NEW CLASS OF HERBICIDE AND NON-GMO CROPS THAT ARE RESISTANT TO THE HERBICIDE", and Zhang, et al., Ser. No. 16/718,293, filed Dec. 18, 2019, entitled "INHIBITION OF EXOCYTOSIS AND THE USES THEREOF", the contents of which are incorporated here by reference in its entirety.

In some illustrative embodiments, this disclosure relates to a method of weed control for a field of a plant comprising the step of applying a cellulose biosynthesis inhibitor selected from the group consisting of ES20 and ES20-1~ES20-9 of FIG. 1A, or a salt thereof, in combination with one or more other herbicides selected from the group consisting of isoxaben, flupoxam and indaziflam, together with one or more diluents, excipients or carriers, to a field in need of said weed control.

In some illustrative embodiments, this disclosure relates to a method of weed control for a field of a plant as disclosed herein, wherein said cellulose biosynthesis inhibitor and other herbicides are applied to a field of a plant together as a mixture of preformulated single product.

In some illustrative embodiments, this disclosure relates to a method of weed control for a field of a plant as disclosed herein, wherein said cellulose biosynthesis inhibitor and other herbicides are applied to a field of a plant separately as an individually pre-formulated product, consequentially or concurrently.

In some illustrative embodiments, this disclosure relates to a method of weed control for a field of a plant as disclosed herein, wherein said plant is resistant to said cellulose biosynthesis inhibitor selected from the group consisting of ES20 and ES20-1~ES20-9 of FIG. 1A, or a salt thereof.

In some illustrative embodiments, this disclosure relates to a method of weed control for a field of a plant as disclosed herein, wherein said plant is a crop for food or feed.

In some illustrative embodiments, this disclosure relates to a composition for weed control of a plant field comprising a cellulose biosynthesis inhibitor selected from the group consisting of ES20 and ES20-1~ES20-9 of FIG. 1A, or a salt thereof, and one or more other herbicides selected from the group consisting of isoxaben, flupoxam and indaziflam, together with one or more diluents, excipients or carriers.

In some illustrative embodiments, this disclosure relates to a composition for weed control of a plant field as disclosed herein, wherein said cellulose biosynthesis inhibitor and other herbicides are applied to a field of a plant together as a mixture of preformulated single product.

In some illustrative embodiments, this disclosure relates to a composition for weed control of a plant field as disclosed herein, wherein said cellulose biosynthesis inhibitor and other herbicides are applied to a field of a plant separately as an individually pre-formulated product, consequentially or concurrently.

In some illustrative embodiments, this disclosure relates to a composition for weed control of a plant field as disclosed herein, wherein said cellulose biosynthesis inhibitor and other herbicides are applied to a field of a plant together with another herbicide of the same or different mode of action.

In some illustrative embodiments, this disclosure relates to a method for treatment or prevention of an infection through inhibition of biofilm formation of microorganisms comprising the step of applying a therapeutic effective amount of a cellulose biosynthesis inhibitor selected from the group consisting of ES20 and ES20-1~ES20-9 of FIG. 1A, or a salt thereof, in combination with one or more other commonly used antibiotics.

In some illustrative embodiments, this disclosure relates to a method for treatment or prevention of an infection through inhibition of biofilm formation of microorganisms as disclosed herein, wherein said treatment of an infection is for the treatment of a human subject or an animal with an infection involving a bacterium having the capability of forming a biofilm during said infection.

In some illustrative embodiments, this disclosure relates to a method for treatment or prevention of an infection through inhibition of biofilm formation of microorganisms as disclosed herein, wherein said infection of a human subject or an animal comprises blood infections, urinary tract infections, lung infections, tooth infections, ear infections, and oral cavity infections.

In some illustrative embodiments, this disclosure relates to a method for treatment or prevention of an infection through inhibition of biofilm formation of microorganisms as disclosed herein, wherein said prevention of an infection is for pre-treatment of a surgical utensil or a medical device which comes in close contact with the tissue of a human or an animal subject.

In some illustrative embodiments, this disclosure relates to a method for treatment or prevention of an infection through inhibition of biofilm formation of microorganisms as disclosed herein, wherein said cellulose biosynthesis inhibitor is ES20 or ES20-1 of FIG. 1A.

In some illustrative embodiments, this disclosure relates to a pharmaceutical composition for treatment or prevention of an infection through inhibition of biofilm formation of microorganisms comprising cellulose biosynthesis inhibitor consisting of ES20 and ES20-1 ES20-9 of FIG. 1A, or a salt thereof, in combination with one or more other commonly used antibiotics.

In some illustrative embodiments, this disclosure relates to a pharmaceutical composition for treatment or prevention of an infection through inhibition of biofilm formation of microorganisms as disclosed herein, wherein said cellulose biosynthesis inhibitor is ES20 or ES20-1.

Cellulose is a polymer of β(1,4)-D-glucose that forms microfibrils with high tensile strength through Van der Waals forces and hydrogen bonds. Cellulose is a major component of the plant cell wall that determines cell shape and overall plant architecture. In plants, cellulose is synthesized by plasma membrane (PM)-localized rosette-structured cellulose synthase (CESA) complexes (CSCs) (Arioli et al., Science 1998, 279, 717-720; Giddings et al., J. Cell Biol. 1980, 84, 327-339). Each CSC consists of 18 CESA units comprising three different isoforms at a 1:1:1 ratio (Hill et al., Plant Cell 2014, 26, 4834-4842; Purushotham et al., Science 2020, 369(6507): 1089-1094). Although CSCs function at the PM, rosette-structured CSCs are present at the Golgi, post-Golgi vesicles, and the PM. In addition, fluorescently labeled CESA localizes to the Golgi, CSC-containing vesicles known as microtubule-associated CESA compartments (MASCs) or small CESA compartments (SmaCCs), and the PM (Gutierrez et al., Nat. Cell Biol. 2009, 11, 797-806). CSCs are thought to be assembled at the endoplasmic reticulum (ER) and transported to the PM through vesicle trafficking, a process facilitated by multiple CESA-interacting proteins and the cytoskeleton (Zhang et al., Plant Physiol. 2016, 179, 1537-1555; Zhang et al., Nat. Commun. 2019, 7, 11656).

Some bacteria, mainly of the genera *Acetobacter, Sarcina*, and *Agrobacterium*, also produce cellulose to form a structure known as biofilm (Ross et al., Microbiol. Rev. 1991, 55, 35-58). Bacterial cellulose has lower levels of crystallinity than plant cellulose and can be produced at high purity, making it valuable for food production, with medical and industry applications. Bacterial cellulose is synthesized by an operon complex consisting of at least three subunits: bacterial cellulose synthase A (BcsA), BcsB, and BcsC (Morgan et al., Nat. Struct. Mol. Biol. 2014, 21, 489-496; McNamara et al., Annu. Rev. Biochem. 2015, 84, 895-921). BcsA, the catalytically active component, localizes to the inner membrane, where it utilizes UDP-glucose to synthesize the glucan chain of cellulose; BcsB is a periplasmic protein that is anchored to the inner membrane via a single C-terminal trans-membrane domain; and BcsC localizes to the outer membrane, but its function is not well understood.

Analysis of the crystal structure of *Rhodobacter sphaeroides* BcsA (RsBcsA) showed that the catalytic residues include conserved DDG, DXD, TED, and QXXRW motifs that are required for cellulose biosynthesis activity (Morgan et al., Nature, 2013, 493, 181-186). Key catalytic motifs in BcsA are conserved in cellulose synthases across kingdoms; for example, plant cellulose synthases contain the same conserved catalytic motifs as BcsA (Pear et al., Proc Natl Acad Sci USA, 1996, 93, 12637-12642). Recently identified atomic resolution structures for plant cellulose synthase revealed that the plants and bacteria use the same catalytic motifs in their cellulose synthases to catalyze cellulose biosynthesis (Purushotham et al., 2020).

We recently identified a cellulose biosynthesis inhibitor named ES20 that likely targets the catalytic site of AtCESA6 and interferes with the subcellular trafficking of the CSC (Huang et al., Plant Cell, 2020, 32, 2141-2157). Here, to identify a more potent analog of ES20, we screened over 600 ES20 analogs for inhibitory effects on plant growth. We identified nine active analogs (ES20-1 to ES20-9), among which ES20-1 more strongly inhibited plant growth and cellulose biosynthesis compared to ES20. We characterized the effects of ES20-1 at the genetic, biochemical, and cellular levels, finding that ES20-1 has the same mode of action as ES20 but is more potent. Previously identified mutants that have reduced sensitivity to ES20 in growth show reduced sensitivity to most of the active ES20 analogs in growth except ES20-6 and ES20-8, indicating these two analogs may have different mode of actions than ES20 and other active analogs. When we perform molecular docking analysis using modeled full-length AtCESA6 structure, we identified another possible target site for both ES20 and ES20-1 at the transmembrane regions in addition to the catalytic site, indicating ES20 and ES20-1 may have more than one binding site on AtCESA6. Notably, both ES20 and ES20-1 inhibited cell growth and cellulose production in the bacterium *Komagataeibacter xylinus* (previously named *Gluconacetobacter xylinus*). These findings highlight the excellent potential of using the ES20 and analogs to inhibit cellulose biosynthesis in plants, and probably also in bacteria, to help uncover the underlying mechanisms of how cellulose catalytic synthesis, cellulose translocation across the PM, and CSC subcellular transport are coordinated during growth and response to environment.

Screening and Identification of Active ES20 Analogs.

ES20 inhibits *Arabidopsis thaliana* root growth by more than 50% at a concentration of 1 µM (Huang et al., 2020). To identify ES20 analogs that more strongly inhibit plant growth and cellulose biosynthesis, we searched for compounds that share similar chemical structures with ES20. We identified 652 analogs that share more than 80% similarity with ES20 in terms of structure and tested their inhibitory effects on *Arabidopsis* Col-0 root growth.

Figure 1D:
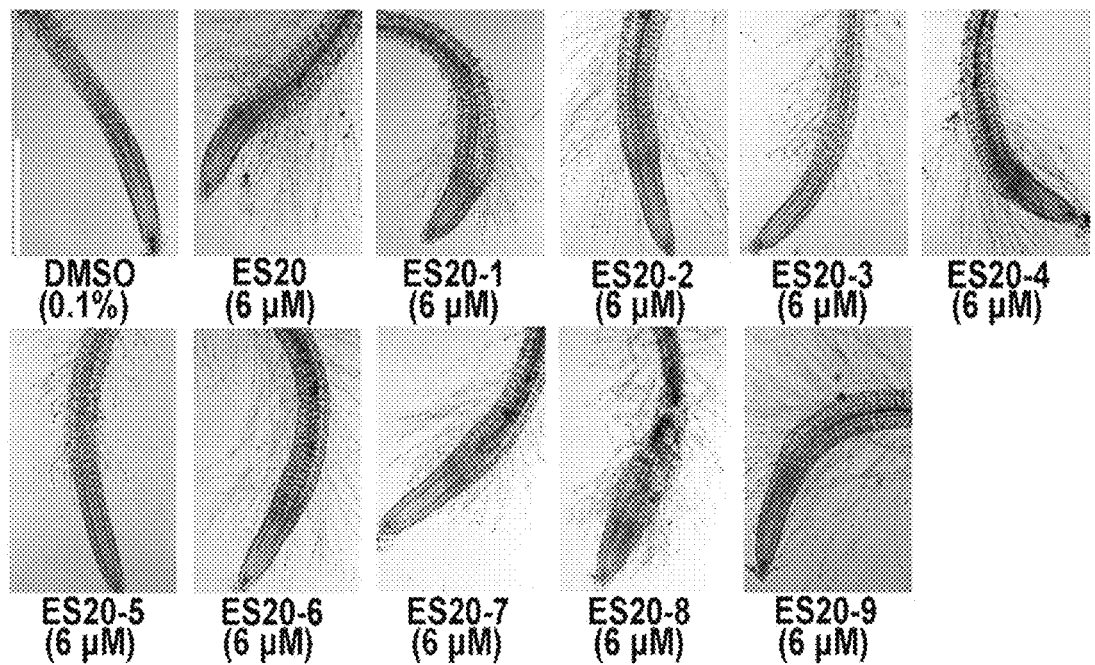
Figure 1E:
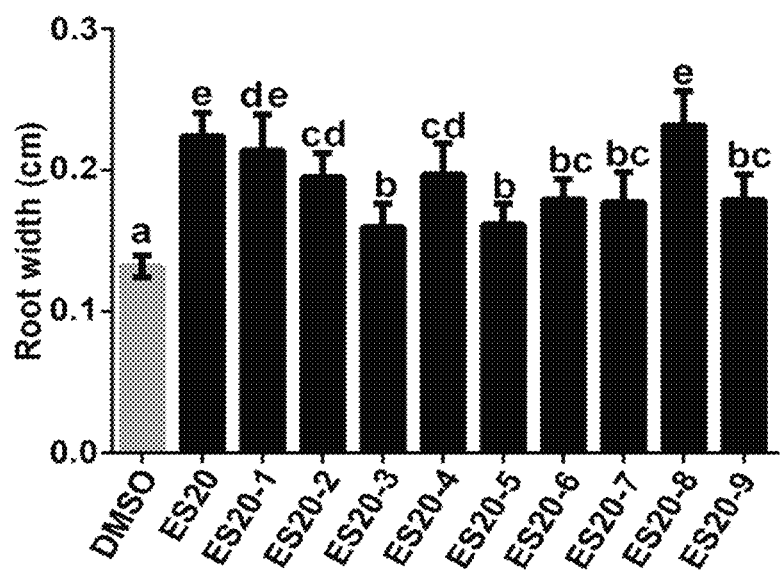
Figure 1F:
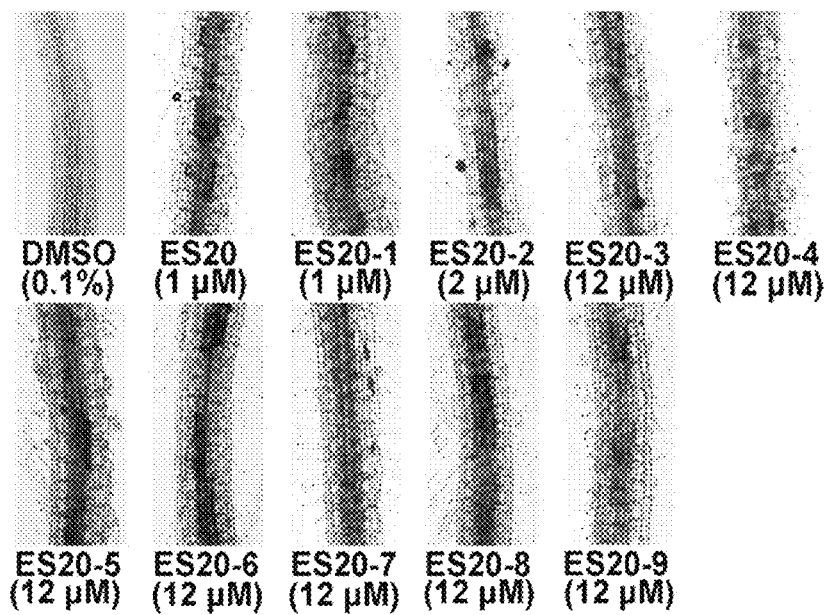
Figure 1G:
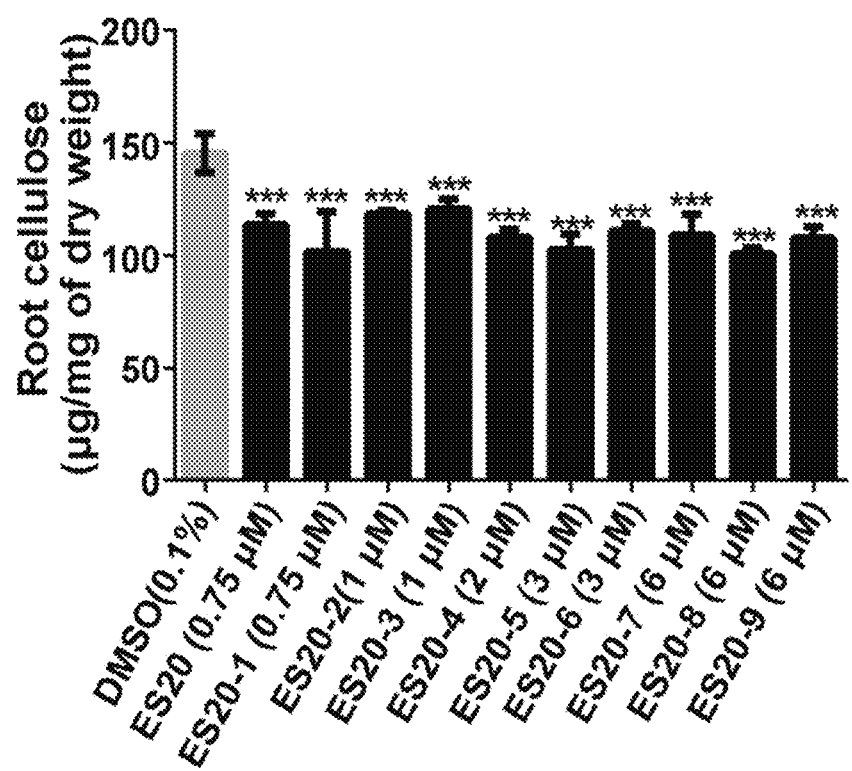

During the primary screening, we sowed Col-0 seeds on solid growth medium supplemented with 0.1% DMSO or 3 mg/L of different compounds with molar concentrations ranging from 5-10 µM. After 7 days of growth, we imaged the seedlings and evaluated the inhibitory effect of each chemical. Because disrupting cellulose biosynthesis by treating plants with a cellulose biosynthesis inhibitor or introducing mutations in the cellulose biosynthesis pathway often leads to root growth inhibition, root swelling, as well as ectopic lignin accumulation (Arioli et al., Science 1998, 279, 717-720; Huang et al., 2020), we first evaluated the ability of the compounds to inhibit root growth and cause root swelling. We identified nine ES20 analogs that caused significantly inhibited root growth and root swelling at 3 mg/L, which we named ES20-1 to ES20-9 (FIG. 1A-1E). We next tested whether these analogs cause ectopic lignin accumulation like ES20. Phloroglucinol staining of seedlings treated with these analogs show obvious accumulation of lignin in root cells, similar to seedlings treated with ES20 (FIG. 1F). Since all nine ES20 analogs inhibit root growth, cause root swelling, and induce ectopic lignin accumulation, we tested whether they inhibit cellulose biosynthesis as well. We grew wildtype seedlings on growth medium supplemented with DMSO (0.1%) or different concentrations of ES20 analogs for 7 days and quantified the crystalline cellulose content in root cell wall. As shown in FIG. 1G, similar to seedlings grown in the presence ES20, seedlings grown in ES20 analogs also have reduced cellulose content in their cell wall. Taken together, ES20-1 to ES20-9 are active ES20 analogs that inhibit plant cellulose synthesis.

Figure 2A:
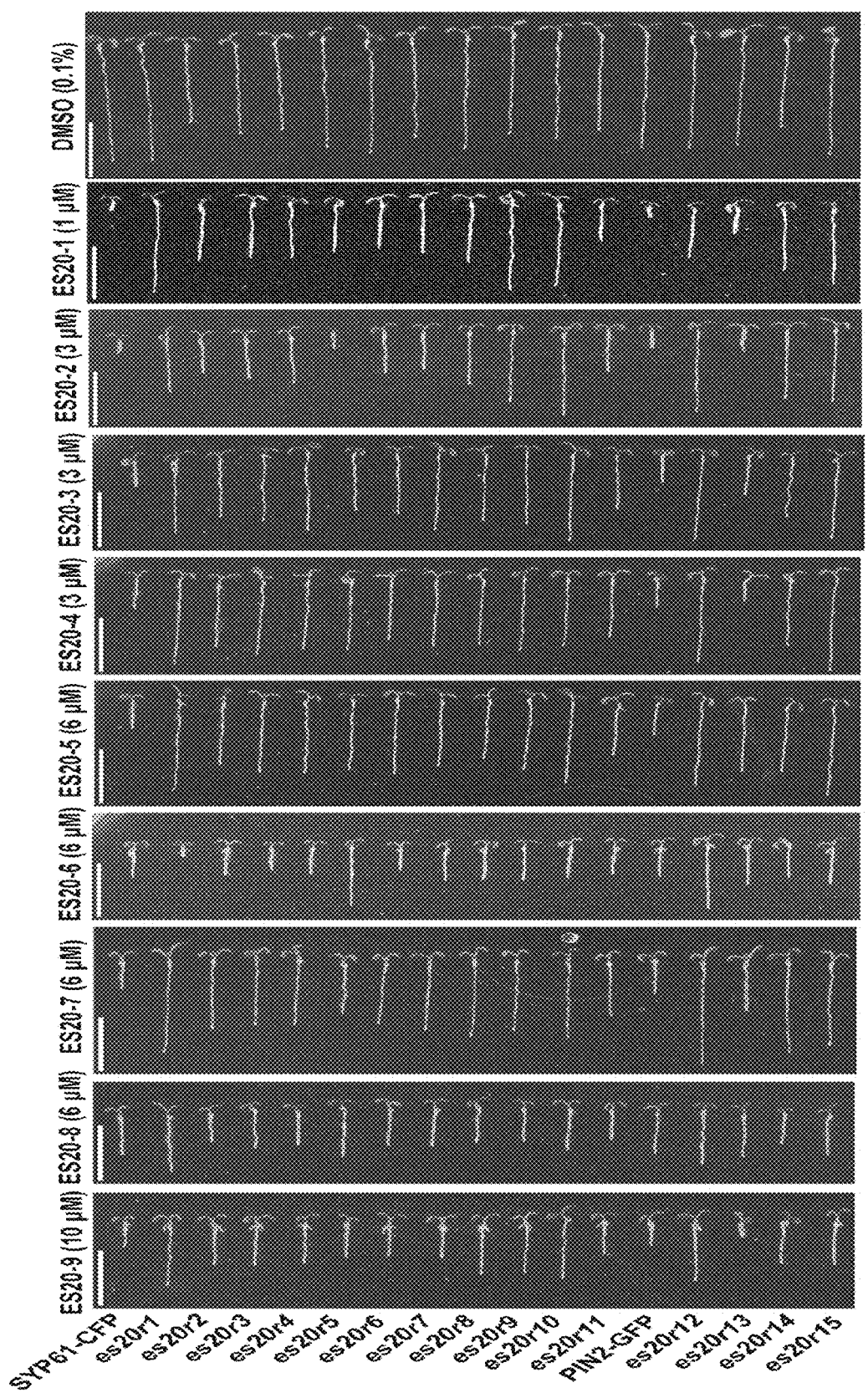
FIGS. 2A-2B. Root growth of EMS-induced mutants with reduced sensitivity to ES20 and transgenic plants expressing AtCESA6 with mutations at the catalytic site in prc1-1 on medium supplemented with active ES20 analogs.

A subset of active ES20 analogs likely target the catalytic domain of AtCESA6. We previously identified 15 Ethyl methanesulfonate (EMS)-induced cesa6 alleles (es20r1-es20r15) that carry missense mutations in AtCESA6 and observed that they had reduced sensitivity to ES20 treatment (Huang et al., 2020). Transgenic plants expressing AtCESA6 carrying missense mutations in the predicted catalytic site in the null cesa6 allele prc1-1 background also had reduced sensitivity to ES20 (Huang et al., 2020). Since ES20 and the nine active ES20 analogs share highly similar structures, we reasoned whether these active analogs target AtCESA6 as well. We therefore examined the growth of es20r1-es20r15 plants in the presence of nine active ES20 analogs compared to wild-type plants. All 15 mutants, which show reduced sensitivity to ES20, also showed reduced sensitivity to ES20-1, ES20-3, ES20-5 and ES20-7, indicating these four analogs may have the same target site on AtCESA6 as ES20 (FIG. 2A). While most of the mutants that have reduced sensitivity to ES20 also have reduced sensitivity to ES20-2, we found that es20r5 and es20r13 have similar sensitivity to ES20-2 compared with control plants SYP61-CFP and PIN2-GFP, indicating ES20-2 may have a slightly different mode of action than ES20 (FIG. 2A). Also, 14 out of 15 mutants except es20r13 show reduced sensitivity to ES20-4 and ES20-9, indicating these two analogs may have a slightly different mode of action than ES20 as well (FIG. 2A). We found that most of the 15 EMS mutants did not show significantly reduced sensitivity to ES20-6 and ES20-8, with only es20r5 and es20r12 show reduced sensitivity to ES20-6 and only es20r1 and es20r5 show slightly reduced sensitivity to ES20-8 (FIG. 2A). Various sensitivity of the mutants to different analogs indicates that although these analogs share very similar structure and inhibit cellulose synthesis, they may have different mode of actions.

Figure 2B:
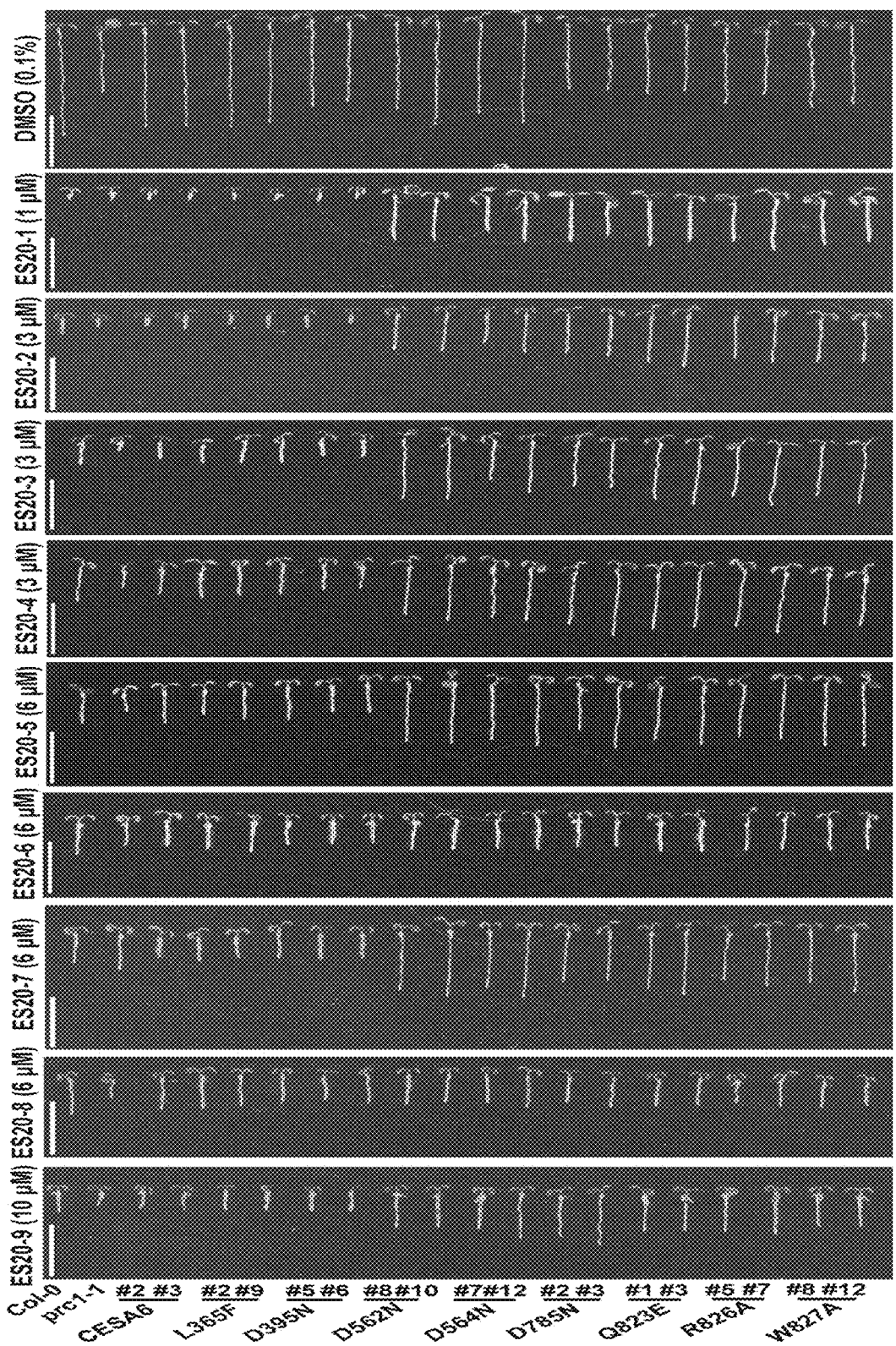

We then examined whether transgenic plants expressing AtCESA6 with predicted missense mutations at the catalytic site in prc1-1 background would have altered sensitivity to active ES20 analogs. Six transgenic lines expressing AtCESA6 carrying missense mutations at the catalytic site (D562N, D564N, D785N, Q823E, R826A, and W827A) showed reduced sensitivity to most of the analogs except ES20-6 and ES20-8 (FIG. 2B). However, the responses of two transgenic lines expressing AtCESA6 carrying missense mutations outside of the catalytic site (L365F and D395N) to nine active ES20 analogs were similar to those of wild-type plants (FIG. 2B). Reduced sensitivity of transgenic plants expressing AtCESA6 carrying missense mutations at the catalytic site to ES20-1, ES20-2, ES20-3, ES20-4, ES20-5, ES20-7, and ES20-9 indicate these analogs may share some similar aspects in their mode of action. In contrary, the normal response of these transgenic plants to ES20-6 and ES20-8 indicates that ES20-6 and ES20-8 are likely to have different mode of action than ES20 and other active analogs. Thus, the response of EMS mutants that display reduced sensitivity to ES20 and transgenic plants that express AtCESA6 carrying missense mutations at the catalytic site to different analogs indicates that ES20-1, ES20-3, ES20-5, and ES20-7 are likely to target the catalytic site as that of ES20; ES20-2, ES20-4, and ES20-9 may have similar target site as ES20 with a slight difference; ES20-6 and ES20-8 are likely to have a different mode of action than ES20 and the other seven active analogs.

ES20-1 is More Potent than ES20 and has the Same Mode of Action as ES20.

Figure 3A:
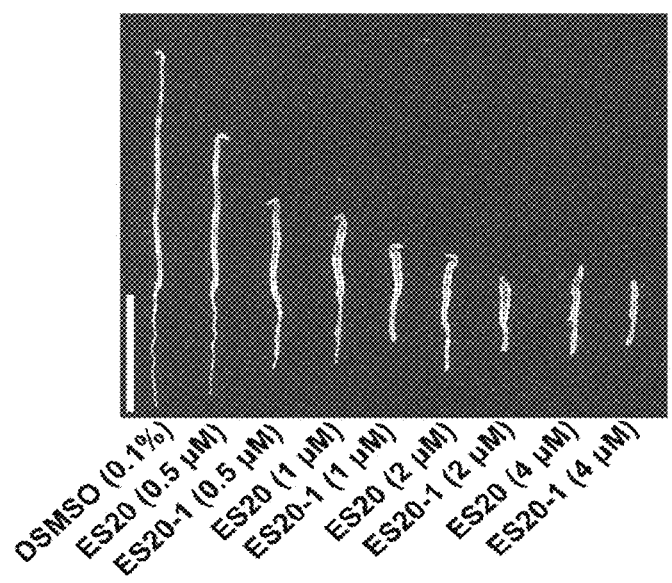
FIGS. 3A-3Q. ES20-1 is more potent than ES20 in inhibiting plant growth and cellulose biosynthesis and targets AtCESA6 directly.
Figure 3B:
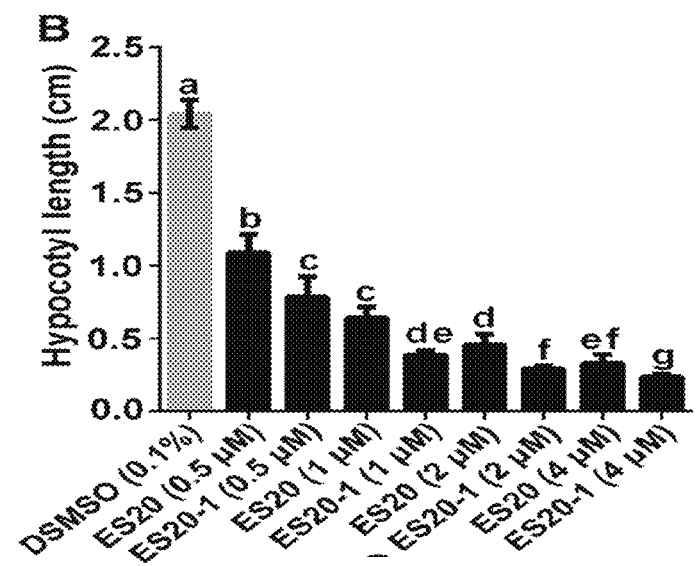
Figure 3C:
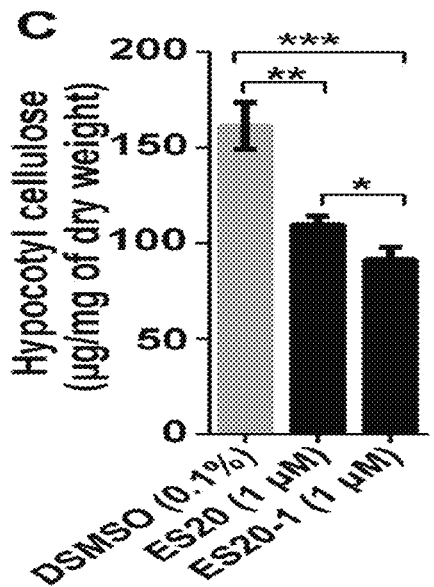

Among nine active ES20 analogs, ES20-1 shares a highly similar structure with ES20 except that it lacks a methoxy group at the left benzene ring, whereas others have different modifications on both the benzene ring and carbonothioyl structure (FIG. 1A). Also among these active analogs, only ES20-1 more strongly inhibited root growth than ES20 at the same dosage (FIGS. 1B and 1C), whereas all nine analogs caused significant root swelling at a concentration of 6 µM (FIG. 1D-1E). ES20-1 is also very potent in inhibiting cellulose biosynthesis in roots (FIG. 1G). Comparison of different parameters caused by nine analogs indicates that ES20-1 is likely to be a more potent analog that can be more valuable in research and in agricultural applications. We thus performed more test to compare the effects of ES20 and ES20-1 and to test the mode of action of ES20-1. We first compared the potency of ES20 and ES20-1 on inhibiting Col-0 hypocotyl growth in the dark. Similar to its effect on roots, ES20-1 inhibited hypocotyl growth more strongly than ES20 at the dosages examined (FIGS. 3A and 3B). We then tested whether ES20-1 is a more potent inhibitor of cellulose biosynthesis than ES20. We grew Col-0 seedlings on solid growth medium supplemented with 0.1% DMSO, 1 µM ES20, or 1 µM ES20-1 in the dark and quantified the crystalline cellulose content in the hypocotyl cell wall. As shown in FIG. 3C, 1 µM ES20 treatment reduced crystalline cellulose levels in the hypocotyl by approximately 35%, from 163±12 µg/mg (mean±SD, n=3 biological replicates) to 109±4 µg/mg (mean±SD, n=3 biological replicates). By contrast, ES20-1 treatment reduced cellulose levels in the hypocotyl by ~45% to a level of 90±6 µg/mg (mean±SD, n=3 biological replicates). Thus, the crystalline cellulose content in the cell wall of dark-grown plants is also more significantly reduced by ES20-1 than the same dosage of ES20 (FIG. 3C), indicating ES20-1 is a more potent cellulose biosynthesis inhibitor than ES20 in *Arabidopsis*.

ES20 has broad spectrum inhibitory effect on the growth of both dicotyledonous and monocotyledonous plants (Huang and Zhang, *Plant Signal Behav.* 2020, 15, 1780039). We tested whether ES20-1 has stronger inhibitory effect on the growth of monocotyledon plants than ES20. We grew rice (*Oryza sativa*) and maize (*Zea mays*) seedlings on the same concentrations of ES20 and ES20-1 and compared their effects on growth. As shown in FIG. 3D-3G, both ES20 and ES20-1 could inhibit the root growth of rice and maize. However, the degree of growth inhibition by ES20-1 is much stronger than that of the same dosage of ES20 (FIG. 3D-3G). These results further confirm that ES20-1 is a more potent general plant growth inhibitor than ES20.

Figure 3H:
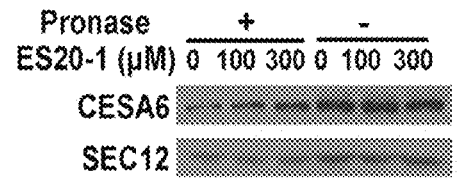
FIG. 3H and I. ES20-1 interacts with AtCESA6 in a DARTS assay.
Figure 3I:
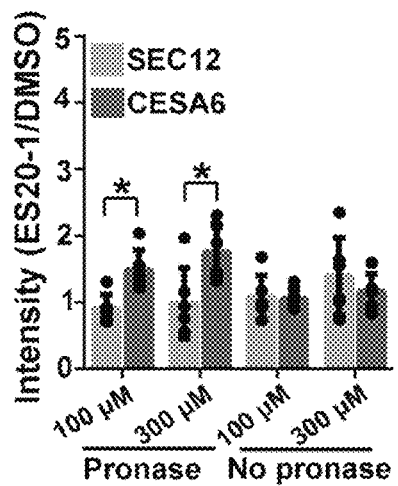
FIG. 3I. Quantitative analysis of the band intensity of YFP-AtCESA6 and SEC12 in ES20-1-treated samples divided by that of DMSO-treated samples in the DARTS assay described in FIG. 3H. Data represent mean±SD (n=6 biological replicates).
Figure 3N:
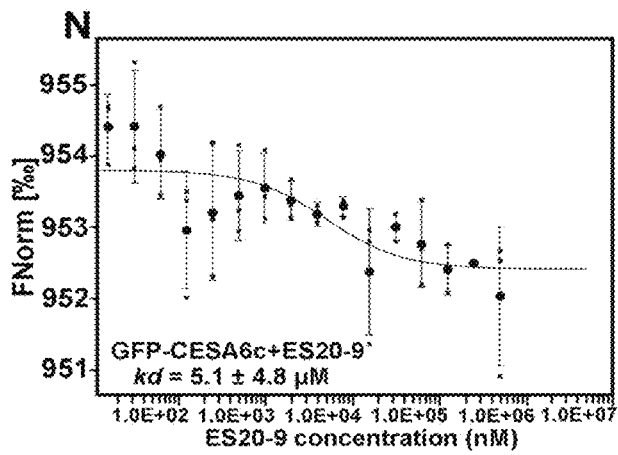
Figure 3O:
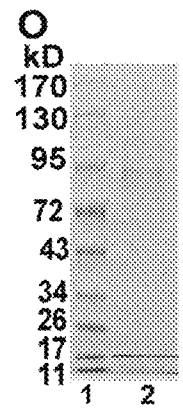
Figure 3P:
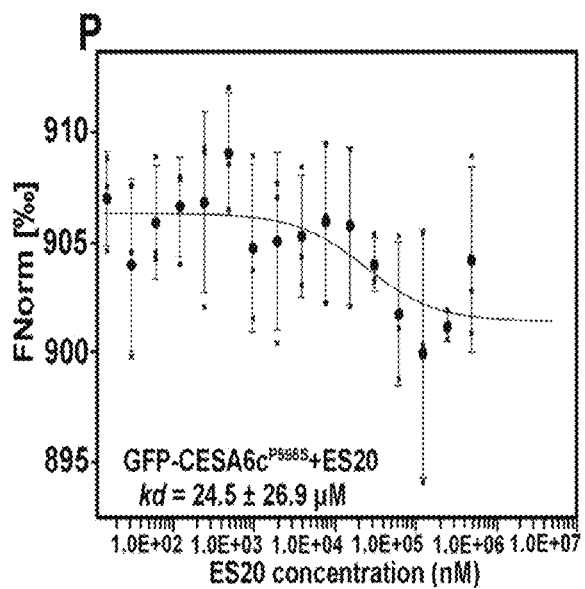
Figure 3Q:
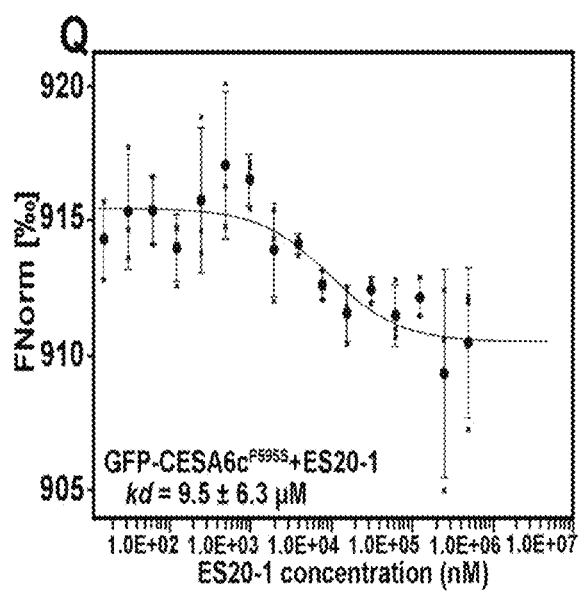
Figure 5A:
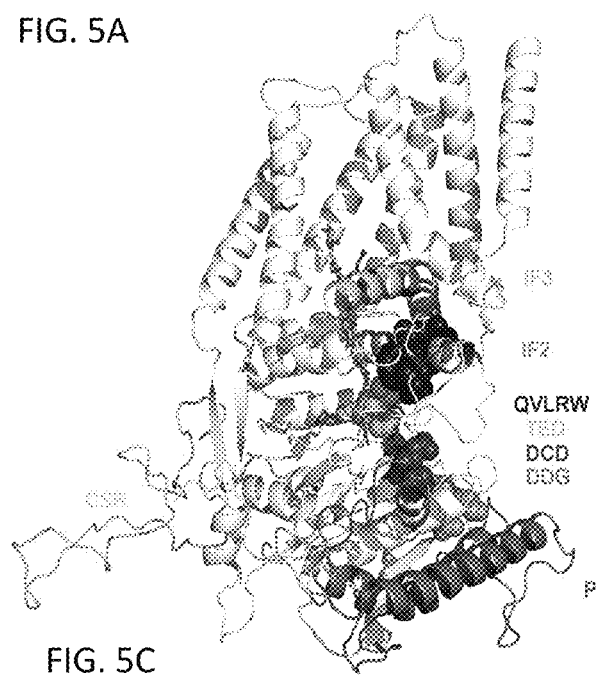
FIGS. 5A-5D. Molecular docking analysis indicates ES20-1 and ES20 share the same binding sites on AtCESA6.
Figure 5B:
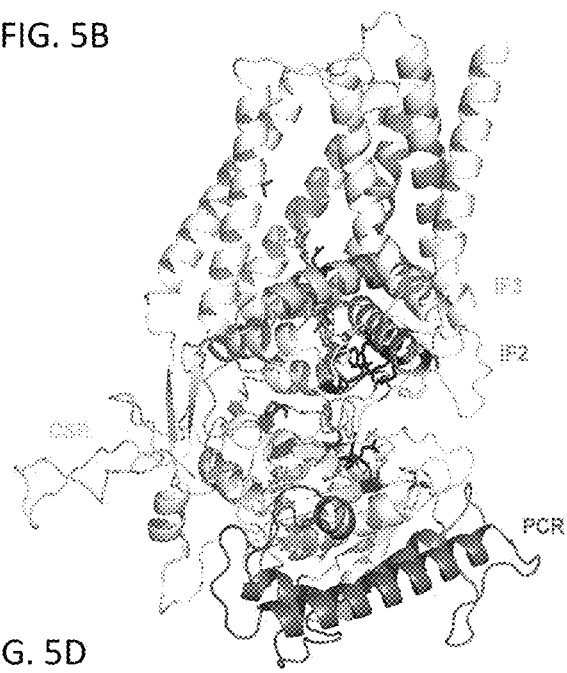
Figure 5C:
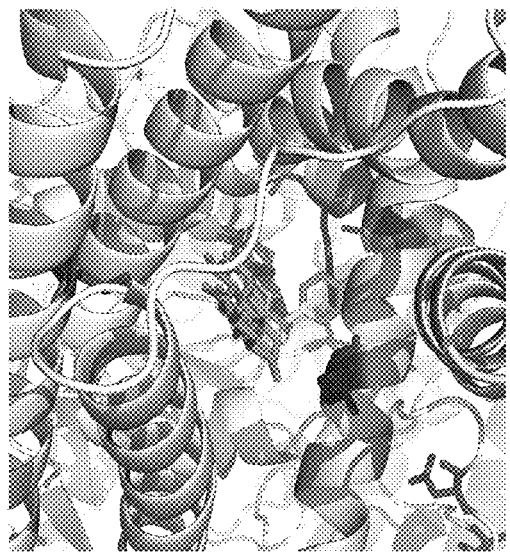
Figure 5D:
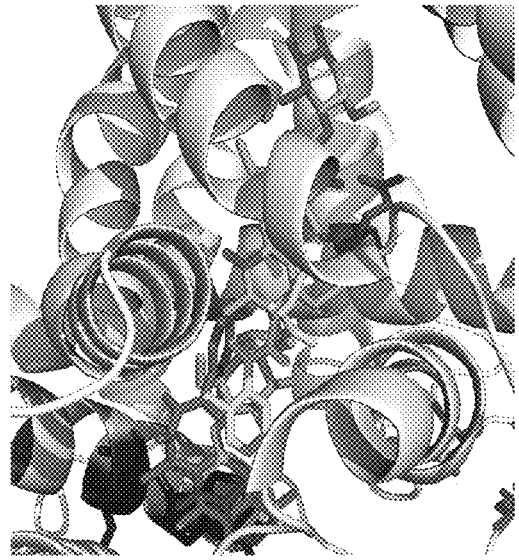

To further validate that ES20-1 targets AtCESA6, we looked for a direct interaction between ES20-1 and AtCESA6. We performed a DARTS (Drug Affinity Responsive Target Stability) assay to test the interaction of ES20-1 with endogenous AtCESA6. We incubated total protein from YFP-AtCESA6 seedlings with either DMSO (as a control) or ES20-1 and digested the mixtures with protease. After protease digestion, higher levels of YFP-AtCESA6 were detected in samples incubated with ES20-1 vs. DMSO, indicating that ES20-1 interacts with endogenous AtCESA6 and protects it from degradation (FIGS. 3H and 3I). We also purified the central cytosolic domain of AtCESA6 (CESA6c) from *E. coli* (FIG. 3J) and performed a Microscale thermophoresis (MST) assay to test its interaction with ES20-1. As shown in FIG. 3K to 3M, CESA6c interacted with ES20, ES20-1, and UDP-glucose, the substrate used for cellulose synthesis. By contrast, the negative control ampicillin did not interact with CESA6c, as shown by the flat binding curve. Therefore, genetic evidence as well as biochemical binding assays strongly suggest that ES20-1 targets AtCESA6 in the same manner as ES20. We found that CESA6c also interacts with another active analog, ES20-9 in MST assay, although the binding affinity is slightly lower than ES20-1 (FIG. 3N). We purified AtCESA6 central cytoplasmic domain carrying missense mutation P595S (CESA6c$^{P595S}$) and tested its interaction with ES20 and ES20-1 (3O). We found that although es20r10 (CESA6$^{P595S}$) plants have reduced sensitivity to both ES20 and ES20-1 in growth (FIG. 2A), CESA6c$^{P595S}$ interacts with both ES20 and ES20-1 in MST assay (FIGS. 3P and 3Q). The interactions of CESA6c with ES20-9 and CESA6c$^{P595S}$ with ES20 and ES02-1 indicates that the interaction of CESA6c with small molecules that may involve multiple amino acid residues.

ES20-1 Interferes with the Trafficking of the CSC to the Plasma Membrane

We recently reported that ES20 treatment reduces the motility and density of CSCs at the PM and induces their accumulation at the SmaCCs and Golgi (Huang et al., 2020). To explore whether ES20-1 affects CSC trafficking in a similar manner to ES20, we examined the effects of ES20-1 on the motility of CSCs. We soaked 5-day-old light-grown YFP-AtCESA6 seedlings in liquid growth medium supplemented with 0.1% DMSO or 6 µM ES20-1 for 30 min and collected time-lapse images of epidermal cells in the root elongation zone by spinning-disk confocal microscopy (SDCM). Analysis of the time-lapse images indicated that the velocity of CSC particles at the PM decreased by ~35% in ES20-1 treated samples vs. the control, from 141.5±3.7 nm/min (mean±SE, n=325 CSC particles from 6 seedlings) to 91.0±3.0 nm/min (mean±SE, n=325 CSC particles from 6 seedlings) (FIG. 4A-4C). In addition to CSC motility, we also examined the effect of ES20-1 on the abundance of CSC at the PM. After 10 min of treatment with 6 µM ES20-1, the abundance of CSCs at the PM decreased by ~30%, from 0.93±0.03 particle/µm$^2$ (mean±SE, n=32 cells from 16 seedlings) to 0.64±0.03 particle/µm$^2$ (mean±SE, n=32 cells from 16 seedlings) (FIGS. 4D and 4E).

We also analyzed the abundance of SmaCCs at the cortical region in the root elongation zone in light-grown seedlings treated with 0.1% DMSO or 6 µM ES20-1. As shown in FIGS. 4F and 4G, ES20-1 treatment clearly increased the accumulation of SmaCCs (red circles) compared to the DMSO control. The abundance of SmaCCs increased by ~30%, from 5.45±0.30 particle/100 µm$^2$ (mean±SE, n=24 cells from 12 seedlings) to 7.07±0.34 particle/100 µm$^2$ (mean±SE, n=24 cells from 12 seedlings) after 10 min of 6 µM ES20-1 treatment (FIGS. 4F and 4G). ES20 treatment reduced the delivery rate of CSCs to PM (Huang et al. 2020). We also analyzed the delivery rate of CSCs to PM using fluorescence recovery after photobleaching (FRAP) assay in root elongation zone of light-grown seedlings treated with 0.1% DMSO or 6 µM ES20-1. As shown in FIGS. 4H and 4I, ES20-1 treatment reduced the delivery rate of CSC to PM compared with DMSO control. The CSC delivery rate of ES20-1 treated seedlings were reduced by ~35%, from 2.19±0.21 particle/µm$^2$/h to 1.41±0.19 particle/µm$^2$/h (mean±SE, n=10 cells from 10 seedlings) after 5 min recovery after photobleaching. Similar to ES20 treatment, 1 h of 6 µM ES20-1 treatment increased the abundance of AtCESA6 at the Golgi (FIGS. 4J and 4K). The integrated fluorescence intensity of Golgi-localized YFP-AtCESA6 signals increased by more than 25% compared to the DMSO control, from 5967.05±194.60 (mean±SE, n=55 Golgi-localized YFP-AtCESA6 from 11 seedlings) to 8684.50±535.60 (mean±SE, n=55 Golgi-localized YFP-AtCESA6 from 11 seedlings), whereas the integrated fluorescence intensity of ManI-CFP expressed in the same cell was not affected by ES20-1 treatment. Thus, at the cellular level, ES20-1 has the same effect on CSC motility, localization, and delivery to the PM as ES20.

We also examined the effect of ES20-1 on the cellular localization of protein that constitutively goes through exocytosis, endocytosis, and recycling and typical organelle marker proteins. We found that after 2 h of 6 µM ES20-1 treatment, the cellular localization of PIN2-GFP is not significantly affected. The cellular localization of organelle marker proteins GFP-PIP2a (PM), GFP-HDEL (ER), VHA-a1-GFP (Trans-Golgi Network/Early Endosome), and YFP-Got1p (Golgi) are not affected. These results show that like ES20, ES20-1 does not affect the localization of general organelle marker proteins and does not disturb the trafficking dynamics of other cargo proteins that go through the secretory pathway after short-term treatment (Huang and Zhang, 2020).

Structural Modeling and Molecular Docking Analysis for Possible ES20-1 Binding Site on AtCESA6

Understanding the binding site of a small molecule on the target protein is important for using the small molecule as a tool to understand the molecular function of the target protein. Previously, we used the crystal structure of RsBcsA as a guide to model the structure of AtCESA6 central cytoplasmic domain (Huang et al., 2020). We then performed molecular docking analysis to predict possible ES20 binding site on modeled structure of AtCESA6 cytoplasmic domain (Huang et al., 2020). We found that ES20 is docked to the catalytic site of AtCESA6 at a similar location as the cellulose biosynthesis substrate UDP-glucose in approximal to the elongating glucan chain (Huang et al., 2020). The reduced sensitivity of plants carrying mutations in amino acids at the catalytic site to ES20 supports our molecular docking prediction (Huang et al., 2020). Atomic resolution structure of full-length *Populus tremulaxtremuloides* CESA8 (PttCESA8) was solved after we reported our structure modeling and molecular docking analysis (Purushotham et al., 2020). In order to predict the possible binding site for ES20-1 on AtCESA6, we performed homology modeling of full-length AtCESA6 structure using the structure of PttCESA8 (PDB: 6WLB) as the template. The modeled structure of AtCESA6 is highly similar to PttCESA8 except at the class-specific region (CSR) where the structural information for PttCESA8 was missing from reported structure determined by cryo-electron microscopy (EM).

We next performed molecular docking analysis using modeled structure of full-length AtCESA6 to identify possible binding site of ES20 and ES20-1 on AtCESA6. For ES20, among nine candidate binding sites with highest confident level, five are close to the elongating glucan chain and amino acids at the catalytic site and interfacial helix 3 (IF3). These candidate binding sites for ES20 are close to what has been predicted when the modeled structure of the central cytoplasmic domain was used for molecular docking analysis (Huang et al., 2020). Many mutations that have caused reduced sensitivity to ES20 in plant growth are in approximal to these predicted binding sites (Huang et al., 2020). When modeled full-length AtCESA6 structure was used for molecular docking analysis, four additional possible binding sites were identified. These four predicted binding sites for ES20 are at the transmembrane regions that is in approximal to the cellulose-conducting channel at the extracellular side of the PM. These candidate binding sites are close to amino acid L286 that is located at the 1$^{st}$ transmembrane region and is close to the cellulose-conducting channel. The mutation L286F causes reduced sensitivity to ES20 in plant growth (Huang et al., 2020). Molecular docking analysis using modeled full-length AtCESA6 structure indicates that ES20 may have an additional binding site at the transmembrane regions in addition to the catalytic site on AtCESA6.

When we performed molecular docking analysis using modeled full-length AtCESA6 and ES20-1, we found that among nine predicted binding sites with highest confidence level, seven are in approximal to the elongating glucan chain and amino acids at the catalytic site and IF3. Two other predicted binding sites for ES20-1 are also located at the transmembrane regions that are close to the cellulose-conducting channel and are next to amino acid L286. We noticed that the predicted binding sites for ES20-1 are very similar to what has been predicted for ES20 (FIG. 5). When we compare the top candidate binding site for ES20 and ES20-1 side by side, we found that the two molecules can be docked to very similar regions in AtCESA6 (FIG. 5). Our molecular docking analysis using modeled full-length AtCESA6 structure indicates that ES20 and ES20-1 can be docked to very similar regions in AtCESA6 and both molecules may target both the catalytic site and the transmembrane regions that are close to the cellulose-conducting channel on AtCESA6.

Both genetic analysis and molecular docking analysis are useful tools in understanding possible mode of actions of small molecules, although a high-resolution three-dimensional co-crystallization structural analysis provides a more definitive mode of action for small molecules (Schenone et al., 2013, Zheng et al., 2014). Previously, genetic analysis has been used to evaluate the possible mode of action of plant cellulose biosynthesis inhibitors such as C17, flupoxam, and isoxaben (Hu et al., 2016). To compare the difference of genetic analysis and molecular docking analysis in characterizing the possible mode of actions of small molecules, we performed molecular docking analysis for C17, flupoxam, and isoxaben on modeled structure of full-length AtCESA6 to predict the possible binding sites for these molecules and the locations of amino acids that are required for the inhibitory effect of these molecules on plant growth.

Multiple mis-sense mutations in AtCESA1 and AtCESA3 were found to cause reduced sensitivity to C17 in plant growth (Hu et al., Plant Cell. 2016, 28, 2276-2290; Hu et al., Plant Physiol. 2019, 180, 827-836). We first identified the amino acids in AtCESA6 that are homologous to the mutated amino acids in AtCESA1 and AtCESA3 that cause reduced sensitivity to C17. We found that these mutated amino acids are all located at different transmembrane regions close to the extracellular side of the PM. Among the nine predicted C17 binding sites on modeled full-length AtCESA6 structure, two are very close to the mutated amino acids that cause reduced sensitivity to C17 in plant growth when mutated. One of these two predicted binding sites is located in a pocket that involves seven amino acids (S897, V298, S308, P1014, G1017, L877, and A1022) that have caused reduced sensitivity to C17 in plant growth when mutated. Five of the predicted binding sites are close to the elongating glucan chain and are next to the amino acid K950, which is close to the IF3 and cause resistance to C17 in plant growth when mutated (Hu et al., 2016, Hu et al., 2019). Two other predicted binding sites for C17 are close to the CSR region and no mutation around these two sites has been found in this region that has caused altered sensitivity to C17 in growth. Thus, the predicted binding site for C17 on AtCESA6 has the most support from the genetic analysis.

Similar to the mutations in AtCESA1 and AtCESA3 that cause reduced sensitivity to C17 in plant growth, multiple mutations in the transmembrane regions of AtCESA1 and AtCESA3 cause reduced sensitivity to flupoxam (Shim et al., *Front Plant Sci*. 2018, 9, 1152). Molecular docking analysis of possible flupoxam binding site on modeled full-length AtCESA6 indicates that six potential binding sites are located at the cellulose-conducting channel in approximal to the elongating glucan chain. None of the identified mutations that have caused reduced sensitivity to flupoxam in growth are located close to these predicted binding sites. Three additional predicted flupoxam binding sites are located at the transmembrane regions and four mutations that cause reduced sensitivity to flupoxam in plant growth are very close to these predicted binding sites. Among these three predicted binding sites at the transmembrane regions, one is located in a pocket that is surrounded by S308, G1013M, P1014, and G1017, all cause reduced sensitivity to flupoxam in plant growth when mutated (Shim et al., 2018). Thus, the predicted binding site for flupoxam on AtCESA6 shown in FIG. S5D-F has the most support from genetic analysis.

Isoxaben is another cellulose biosynthesis inhibitor that is believed to target cellulose synthases because multiple mutations in different CESA isoforms have been found to cause reduced sensitivity to isoxaben in plant growth (Shim et al., 2018). The homologous amino acids in AtCESA6 that cause reduced sensitivity to isoxaben in plant growth are located at the transmembrane regions on the extracellular side of the PM (R1064, 51002, G1017-AtCESA3G998, R293-AtCESA3R276), in the IF2 (R826-AtCESA3R806), in FXVTXK motif (T962-AtCESA3T942), or right in front of the DDG motif (5394-AtCESA3 S377). All nine predicted binding sites for isoxaben are located at the cellulose-conducting channel in adjacent to the elongating glucan chain. The predicted binding sites are away from the amino acids at the transmembrane regions but six of the predicted binding sites are close to the IF2 containing R826-AtCESA3R806 that causes reduced sensitivity to isoxaben in plant growth when mutated. Thus, the combination of genetic analysis and molecular docking analysis does not provide a more precise prediction on the mode of action for isoxaben.

In theory of drug discovery, when mutations occur in drug target site, it often disrupts the interaction between the drug and the target protein, which will directly cause resistance to the drug. This provides theoretical basis that drug-resistant mutants are likely to carry mutations at the drug target sides. Thus, the locations of mutations that cause reduced sensitivity to small molecules often can guide the prediction of drug binding site on candidate target protein. It has been challenging to perform x-ray crystallography to solve the structures of plant CESAs or to co-crystalize plant CESA with candidate small molecule inhibitors. Here we combined the mutation analysis and the molecular docking analysis to predict possible binding sites for several cellulose biosynthesis inhibitors on modeled structure of full-length AtCESA6. It is likely that ES20 and ES20-1 can target both the catalytic site and the cellulose-conducting channel at the transmembrane regions on extracellular side of the PM. For C17 and flupoxam, each has a predicted pocket at the transmembrane region that is surrounded by multiple amino acids that are required for the inhibitory effect of these two molecules in plant growth, which may likely represent the binding sites for these molecules. For isoxaben, all nine predicted binding sites are located at the cellulose-conducing channel containing elongating glucan chain and six of these predicted binding sites are close to the identified amino acid R826-AtCESA3R806 in IF2 that is required for the inhibitory effect of isoxaben on plant growth. Multiple predicted binding sites in the cellulose-conducting channel indicate that isoxaben might interfere with the glucan chain translocation across the PM that requires coordinated functions of IF2, amino acids at the transmembrane regions at the extracellular side of the PM, and FXVTXK motif.

ES20 and ES20-1 are Active in Bacterial Cells

Like plants, some bacteria (mainly Gram-negative bacteria) also produce cellulose. Bacterial cellulose is an important component of the polymeric matrix in biofilms. Cellulose contributes to the pathogenicity of biofilms, which cause chronic infections, and makes biofilms resistant to the human immune system and antibiotic treatments (Limoli et al., *Microbiol. Spectr.* 2015, 3). Disrupting cellulose biosynthesis by deleting cellulose synthase genes from the bacterial genome leads to reduced biofilm formation in various bacteria (Castiblanco and Sundin, *Mol. Phant Pathol.* 2018, 19, 90-103). Thus, small molecules that inhibit bacterial cellulose production have the potential to interfere with biofilm formation and bacterial host infection. However, to date, there is no report of an efficient bacterial cellulose biosynthesis inhibitor with a known mode of action.

Based on primary protein sequence analysis and a comparison of three-dimensional protein structures, the catalytic sites of cellulose synthases are highly conserved across kingdoms (Huang et al., 2020, Purushotham et al., 2020). The amino acids that are directly involved in glucan chain initiation, elongation, and translocation are conserved between plant and bacterial cellulose synthases (Huang et al., 2020). Based on the conservation of catalytic sites in cellulose synthases, we hypothesized that ES20 and ES20-1 would inhibit bacterial cellulose biosynthesis as well. We chose to test the effects of ES20 and ES20-1 on cell growth and cellulose production in *Komagataeibacter xylinus* (*K. xylinus*, previously known as *Gluconacetobacter xylinus*) because this bacterium produces abundant cellulose. We first tested whether ES20 and ES20-1 affect *K. xylinus* cell growth. We grew *K. xylinus* cells in liquid Hydrosulphite of Sodium (HS) medium and then we inoculated 20 µL of series diluted culture to HS solid growth medium supplemented with DMSO (0.1%) or different concentrations of ES20 and ES20-1. We found that ES20 and ES20-1 inhibit *K. xylinus* cell growth at both 20 µM and 50 µM concentrations, with more significant inhibition at 50 µM (FIG. 6A). We found ES20 and ES20-1 affect *K. xylinus* colony morphology as well. When grown on HS medium supplemented with 0.1% DMSO, the colony shows wrinkles radiating structures whereas the wrinkles are not obvious in colonies grown in the presence of ES20 or ES20-1 (FIG. 6B). Wrinkles radiating structure is often observed in cellulose-producing bacteria strains and this structure is often affected when cellulose biosynthesis is disrupted.

We next grew *K. xylinus* cells in growth medium supplemented with DMSO, ES20, or ES20-1 under agitation. After 5 days of agitated cultivation, visible cellulose clusters formed in all cultures (FIG. 6C). However, these cluster were smaller in cultures containing ES20 and ES20-1 than in cultures containing DMSO (FIGS. 6C and 6D). We also grew *K. xylinus* in liquid medium supplemented with DMSO, ES20, or ES20-1 under static cultivation conditions. Without agitation, pellicles containing cellulose often form at the air-liquid interface. After 5 days of static cultivation, obvious pellicles formed in cultures containing DMSO, ES20 or ES20-1 (FIG. 6E). However, it is obvious that the pellicles in cultures containing DMSO are thicker than the pellicles in cultures containing 20 µM ES20 or 20 ES20-1 (FIG. 6E). To quantify the effects of ES20 and ES20-1 on cellulose production, we harvested the pellicles from these cultures and isolated cellulose from the pellicles. Dried cellulose membranes from the pellicles of cultures containing ES20 and ES20-1 were smaller than those from cultures containing DMSO (FIG. 6F). The yield of dried cellulose from pellicles of 5-day-old cultures containing DMSO was approximately 500 mg/L (FIG. 6G), whereas that from cultures containing ES20 or ES20-1 was significantly lower (FIG. 6G). 20 µM ES20 and 20 µM ES20-1 treatment caused the dry mass of cellulose to decrease by ~45% and 30%, from 504±58 mg/L (mean±SD, n=9 biological replicates) (DMSO) to 268±139 mg/L (mean±SD, n=9 biological replicates) (ES20) and 346±152 mg/L (mean±SD, n=9 biological replicates) (ES20-1), respectively. Therefore, both ES20 and ES20-1 have an inhibitory effect on cell growth and cellulose production in *K. xylinus*.

Endosidin20 Targets Bacterial Cellulose Synthase in Molecular Docking Analysis.

Figure 7:
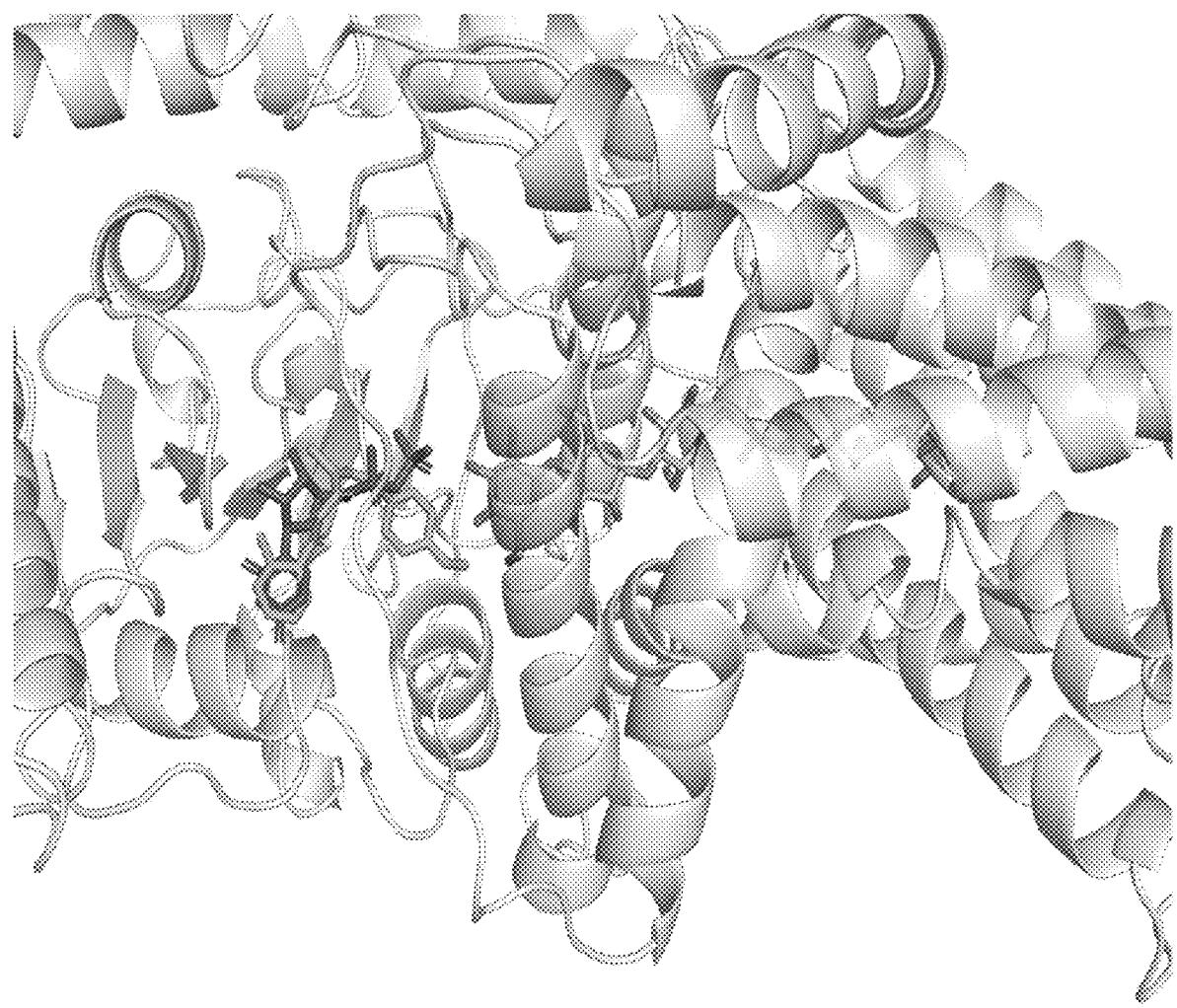
FIG. 7: Endosidin20/Cellulosin targets the catalytic site of RsBcsA in molecular docking analysis. Endosidin20/Cellulosin (Cyan) is docked to the same binding pocket as UDP-glucose (Magenta). The solved structure of RsBcsA (PDB: 4P00) was used for the molecular docking. The locations of UDP-glucose and glucose chain (Red) are from X-ray structure file of RsBcsA.

Previously, through chemical genetic analysis, biochemical assays, molecular docking, and live-cell imaging analysis, we found that Endosidin20/Cellulosin targets the catalytic site of plant cellulose synthase. Because the structure of *Rhodobacter sphaeroidesin* cellulose synthase RsBcsA has been solved, we performed molecular docking analysis to see whether Endosidin20/Cellulosin can target RsBcsA. We found that Endosidin20/Cellulosin can bind to the same pocket as UDP-Glucose, the substrate of cellulose synthase in RsBcsA (FIG. 7). Our molecular docking results show that Endosidin20 can target the catalytic site of RsBcsA.

Endosidin20/Cellulosin Inhibits Bacterial Cell Growth and Cellulose Synthesis.

To test the effect of Endosidin20/Cellulosin in bacterial cell growth, we first grew Rhodobacter sphaeroidesin in the presence of Ensodin20/Cellulosin. We found that after overnight culture, the growth of Rhodobacter sphaeroidesin was significantly slower in media supplemented with Ensodin20/Cellulosin compared with the control media supplemented with DMSO solvent. Our results show that Endosidin20/Cellulosin is active in controlling the growth of bacteria that secrete cellulose.

Understanding and manipulating the biosynthesis of cellulose, the most abundant polymer on Earth, is of critical importance. Cellulose biosynthesis inhibitors (CBIs) are useful not only to study the mechanism of cellulose biosynthesis but also for weed control in agriculture and to treat chronic biofilm infections in humans (Limoli et al., 2015). Among the plant CBIs identified to date, isoxaben, flupoxam and indaziflam have been developed into commercial herbicides, particularly pre-emergent herbicides. In addition, the small molecule Pellicin inhibits cellulose biosynthesis in bacteria, although its mode of action is unknown, which has limited its application in biofilm treatment (Strap et al., PLoS ONE, 2011, 6, e28015).

ES20, a newly identified CBI, shows great promise because unlike other CBIs including isoxaben and indaziflam, its working mechanism is clear, i.e., it targets the catalytic domain of CESA based on genetic, biochemical analyses, and molecular docking analysis results. Here, through molecular docking analysis using modeled full-length AtCESA6 structure guided with an updated plant CESA structure as template, we found that ES20 may target the transmembrane regions that contain cellulose-conducing channel as well. In this study, we identified nine active ES20 analogs from an analog screening. These analogs showed typical CBI effects on plant growth, including root growth inhibition, cell swelling and cellulose biosynthesis inhibition. All of the ES20 insensitive mutants showed reduced sensitivity to ES20-1, ES20-3, ES20-5 and ES20-7, which indicate these analogs may share the same binding site on AtCESA6 as ES20. Interestingly, 14 out of 15 mutants except the es20r13 showed reduced sensitivity to ES20-4 and ES20-9, and 13 out of 15 mutants except es20r5 and es20r13 showed reduced sensitivity to ES20-2, which suggests that ES20-2, ES20-4 and ES20-9 may share very similar but with slightly different target sites on AtCESA6 as ES20. Interestingly, most of the ES20 insensitive mutants have normal sensitivity to ES20-6 and ES20-8, with only es20r5 and es20r13 show reduced sensitivity to ES20-6 and only es20r1 and es20r5 show reduced sensitivity to ES20-8, which indicates that ES20-6 and ES20-8 may inhibit cellulose biosynthesis using a quite different mode of action than ES20 and the other seven active ES20 analogs. Further characterization of ES20-6 and ES20-8 on their mode of action through genetic analysis may reveal new target sites for these two analogs. Because multiple mutations can lead to reduced sensitivity to ES20 and ES20-1, the application of these two compounds as herbicide can be limited, which makes it more interesting to investigate analogs, such as ES20-6 and ES20-8, that can inhibit the growth of these mutants that have reduced sensitivity to ES20 and ES20-1.

ES20-1 is more potent than ES20 in inhibiting plant growth and cellulose synthesis, but it is likely to have the same mode of action as ES20. Based on our updated molecular docking analysis using modeled structure of full-length AtCESA6, both ES20 and ES20-1 may target both the catalytic site and the transmembrane regions of CESA. The chemical structures of ES20 and ES20-1 are quite similar except that ES20-1 does not have a methoxy group at one of its benzene rings. The predicted octanol-water partition coefficient (logP) is very similar between ES20 (2.57) and ES20-1 (2.52), indicating that ES20 and ES20-1 have very similar molecular hydrophobicity. Very similar octanol-water partition coefficient indicates that ES20 and ES20-1 may have very similar membrane permeability. Thus, more potent activity of ES20-1 than ES20 in inhibiting plant growth and cellulose biosynthesis is unlikely due to the difference in their membrane permeability (Bennion et al., J. Phys. Chem. B, 2017, 121, 5228-5237). When we examine the molecular docking results, we found that the predicted binding affinity for ES20-1 with AtCESA6 is much higher than that of ES20, with the mean of nine predicted value of −8.1 Kcal/mol for ES20-1 and −7.0 Kcal/mol for ES20. MST analysis also shows that ES20-1 may have a higher binding affinity to CESA6c than ES20 (FIG. 3K, 3L). Thus, it is possible that increased inhibitory potency of ES20-1 is due to higher binding affinity to AtCESA6. It has been observed previously that minor modifications in chemical structure can lead to enhanced chemical performance (Huang et al., Plant Physiol. 2019, 180, 1756-1770). The increased inhibitory activity of ES20-1 could be quite useful, especially for herbicide development, which could reduce the dosage and cost of agricultural application. The other eight active ES20 analogs are less potent than ES20, but they enriched the toolbox of cellulose biosynthesis inhibitors that are useful in understanding the mechanisms of cellulose biosynthesis. Among these analogs, ES20-6 and ES20-8 seem to have different mode of action than ES20 and other ES20 analogs. It is thus worth further investigation on their mode of action in inhibiting cellulose biosynthesis and use them as complement to ES20 and ES20-1 in agricultural applications.

It is the most challenging task in drug discovery to identify the exact mode of action of candidate small molecules. Multiple approaches, such as biochemical binding assays, bioinformatic analysis, genetic analysis, and crystallography are often applied to characterize the small molecule of interest. In the case of CBIs, although multiple small molecules have been found to inhibit plant cellulose biosynthesis and have been widely used in agricultural production, their mode of actions are not precisely identified. Most of these CBIs are believed to directly target cellulose synthases because missense mutations in CESAs have been found to cause reduced sensitivity to these CBIs. The challenges for characterizing the exact mode of action of these CBIs are mostly due to the difficulty in manipulating CESA proteins in vitro. It is only until recently that the structure of plant CESA was solved through cryo-EM and it still remains a great challenge to solve the structure of full-length plant CESA in a complex with small molecule inhibitors. In this report, we used homology modeling to predict the structure of full-length AtCESA6 and used the molecular docking analysis to predict possible binding sites for ES20, ES20-1, and three other previously published CBIs on modeled structure of full-length CESA6. We also tried to compare the locations of predicted bindings sites and the amino acids that have been found to be essential for the inhibitory effects of the CBIs. We found that some of the predicted binding sites for CBIs are very close to amino acids that have been found to cause reduced sensitivity to these CBIs in plant growth. For example, the predicted binding sites for both ES20 and ES20-1 are located at the regions close to the catalytic site and at the transmembrane regions (FIG. 5). For C17, one of the predicted binding sites on full-length AtCESA6 is supported by seven amino acids that surround the binding pocket, indicating C17 may likely inhibit cellulose biosynthesis by targeting CESAs at the transmembrane regions on the extracellular side of the PM. One of the predicted binding sites for flupoxam is also supported by multiple amino acids that are required for the inhibitory effect of this CBI. It is less clear for isoxaben because most of the amino acids that are required for the inhibitory effect of this CBI are not so close to the predicted binding sites. However, multiple predicted isoxaben binding sites on full length CESA6 are close to IF2 and an amino acid (R826-AtCESA3R806) in IF2 is required for the inhibitory effect of isoxaben. It is possible that isoxaben inhibits efficient translocation of cellulose across the PM, which requires coordinated function of IF2 and amino acids in the transmembrane regions. Although the molecular docking analysis does not provide definite mode of action of CBIs, we expect that the combination of genetic analysis and molecular docking could provide better guidance for selecting corresponding CBIs as tools in investigating the molecular function of plant CESAs. The subcellular trafficking of CSC has been found to be affected by CBIs. Due to non-definitive mode of actions of CBIs, a careful examination of fluorescence-tagged CESA with different mutations are required to define how different domains/motif affect CSC trafficking.

A high-resolution structure of a plant CESA just became available very recently (Purushotham et al., 2020). The important motifs required for cellulose catalytic synthesis and the catalytic core structures are highly conserved among CESAs across kingdoms (Huang et al., 2020). We previously reported that the amino acids in critical catalytic motifs, such as the DDG, DXD, TED, and QXXRW motifs, are required for the inhibitory activity of ES20 (Huang et al., 2020). When the amino acids were mutated, plants became less sensitive to the inhibitory effects of ES20. Here we report that ES20 and ES20-1 inhibit cellulose biosynthesis not only in plants, but also in bacteria. It is likely that ES20 and ES20-1 target BcsA as well. Our previous biochemical and genetic analyses and the growth assay and cell wall analysis in this report support the notion that the cellulose catalytic synthesis process is conserved between plants and bacteria. Notably, ES20-1 inhibited cellulose biosynthesis more strongly than ES20 in plants but shows similar potency in bacteria at the concentrations tested in this study. Therefore, although key catalytic motifs are conserved between plant and bacterial cellulose synthases, minor structural difference may determine that ES20-1 is not more potent than ES20 in bacteria. Although further investigation is required to identify the mode of action of ES20 and ES20-1 in bacteria, they represent valuable potential tools for studying cellulose biosynthesis and biofilm formation in bacteria. It is also possible that ES20, ES20-1, and other analogs could serve as lead compounds for the development of new treatments for chronic biofilm infection in the future.

The following non-limiting exemplary embodiments are included herein to further illustrate the invention. These exemplary embodiments are not intended and should not be interpreted to limit the scope of the invention in any way. It is also to be understood that numerous variations of these exemplary embodiments are contemplated herein.

Material and Methods

Plant Materials, Growth Conditions, and Growth Assays

To test the inhibitory effects of different chemicals on plant growth, wild-type *Arabidopsis* Col-0 plants were used. The seeds of plants used for growth assays or live cell imaging were sequentially sterilized with 50% bleach and 75% ethanol. After washing with sterilized water, the seeds were sown on ½-strength Murashige and Skoog (MS) medium supplemented with 3 mg/L of various chemicals. The plants were grown under continuous light of 130 µmol $m^{-2}$ $s^{-1}$ intensity illuminated by a Philips F25T8/TL841 25-watt bulb at 22° C. To quantify the inhibitory effects of different ES20 active analogs on the root growth of *Arabidopsis* wildtype, EMS mutants, and transgenic plants expressing mutated AtCESA6 in prc1-1 background, sterilized Col-0, mutants, and transgenic plants seeds were sown on gridded Petri plates containing ½-strength MS medium supplemented with different concentrations of ES20 analogs. The plates were placed in vertical orientation in the growth chamber for root measurement. The plates were scanned using an Epson Perfection V550 scanner after 7 days of growth, and the root lengths of plants were quantified using ImageJ software. To test the effects of ES20 analogs on etiolated hypocotyl growth, sterilized Col-0 seeds were sown on ½-strength MS medium supplemented with different concentrations of ES20 analogs. The Petri dishes were wrapped in two layers of aluminum foil and incubated at 22° C. for 7 d. The Petri dishes were scanned, and hypocotyl length was measured using ImageJ. Transgenic plants expressing fluorescence-tagged PIN2, PIP2a, HDEL, VHA-a1, and GOT1p were as reported previously (Xu and Scheres, Plant Cell, 2005, 17, 525-536).

Crystalline Cellulose Content Measurement

*Arabidopsis* Col-0 seeds were sown on growth medium supplemented with 0.1% DMSO, 1 µM ES20, or different concentrations of ES20 analogs. After stratification, the plants were grown in the dark for 7 d. Cellulose extraction and measurement were performed as previously described (Huang et al., 2020).

Lignin Staining

*Arabidopsis* Col-0 seeds were sown on growth medium supplemented with 0.1% DMSO and different ES20 analogs. After stratification, the plants were grown in in the growth chamber under continuous light for 5 days. The root lignin staining was performed as previously described (Huang et al., 2020).

CESA6c Protein Expression and Purification

To obtain the central cytosolic domain of AtCESA6 for the MST assay, we inserted the GFP coding sequence into the SacI and PstI restriction enzyme sites of the pRSF-Duet-1 vector (Huang et al., 2020). The GFP coding sequence was amplified from the pUBN-GFP-DEST vector. The sequence encoding the central cytosolic domain of CESA6 (CESA6c) was amplified from Col-0 cDNA and fused with GFP at the C-terminus. CESA6c construct was used as a template for creating CESA6c$^{P595S}$ construct by site-directed mutagenesis. Protein purification was performed as previously described (Huang et al., 2020).

MST Assays

MST assays were carried out using a Monolith NT.115 (NanoTemper) machine at the Chemical Genomics Facility at Purdue University. Increasing concentrations of ES20-1, UDP-glucose, and ampicillin were titrated against 100 nM GFP-CESA6c protein in standard MST buffer (50 mM Tris, pH 7.5, 150 mM NaCl, 10 mM $MgCl_2$, 0.05% Tween 20). The ES20-1 was dissolved in DMSO, and the final concentration of DMSO was 5% (vol/vol). MST standard capillaries were used to load the samples into the MST instrument.

Triplicate reactions were performed for each test. The MST data were processed using MO. Affinity Analysis Version 2.3 software.

DARTS Assays

To test for an interaction between AtCESA6 and ES20-1 using a DARTS assay, 7-day-old YFP-AtCESA6 light-grown seedlings were harvested and ground to a powder in liquid nitrogen. The ground tissue was homogenized in lysis buffer (50 mM Tris-HCl, pH 7.5, 150 mM NaCl, 0.5% Triton X-100, 2 mM DTT, one tablet/50 mL EDTA free Pierce protease inhibitor [Thermo Fisher]) at 2:1 ratio (2 mL buffer: 1 g tissue). The method used for total protein extraction and the detailed steps of the DARTS assay were described previously (Huang et al., 2020). The X-ray films were scanned, and the signal intensity of each protein band was quantified after background subtraction using Image J. The relative intensities were quantified by dividing the values in ES20-1-treated samples by the values in DMSO-treated samples.

Live-Cell Imaging of Fluorescence-Tagged Marker Proteins

To test the effect of ES20-1 on cellular localization of endomembrane marker proteins, transgenic plants expressing different fluorescence-tagged proteins were grown on ½-strength MS agar plates for 5 d under continuous light. The seedlings were incubated in ½-strength MS liquid media supplemented with 6 μM ES20-1 for 2 h. The images were collected by Zeiss 710 laser scanning confocal microscope equipped with 40×/1.2 NA water objective. For images of GFP-tagged proteins, the 488-nm laser line was used as an excitation source and emission light at 493-598 nm was collected. For images of YFP-tagged proteins, the 514-nm laser line was used as an excitation source and the emission light at 519-621 nm was collected.

Spinning-Disk Confocal Microscopy (SDCM)

For SDCM live cell imaging, seedlings were grown vertically for 5 d, and images were taken from the 2nd or 3rd epidermal cell below the first obvious root hair in the root elongation zone. Two thin strips of double-sided adhesive tape were placed on top of glass slides approximately 2 cm apart. 100 μl of ½-strength MS liquid growth medium containing 0.1% DMSO or 6 μM of ES20-1 was applied to the slide, and seedlings were mounted in the liquid medium. A 22×40 mm cover glass was placed on top of the double-sided tape for imaging. For longer term imaging during CESA velocity analysis, seedlings were mounted on a piece of 1-mm thick 0.6% Phytagel pad affixed to the glass slide to minimize compression and liquid evaporation.

To examine the cellular localization of YFP-AtCESA6 and YFP-AtCESA6; ManI-CFP, SDCM imaging was performed using a CSU-X1-A1 Yokogawa scanning unit mounted on an Olympus IX-83 microscope equipped with a 100×/1.4NA UPlanSApo oil objective (Olympus) and an Andor iXon Ultra 897BV EMCCD camera (Andor Technology). YFP and CFP fluorescence was excited with 515-nm and 445-nm laser lines and emission collected through 542/27-nm and 479/40-nm filters, respectively.

For fluorescence recovery after photobleaching (FRAP) experiments, images were collected using a Zeiss Observer Z.1 microscope, equipped with a Yokogawa CSU-X1 head and a 100×/1.46 NA PlanApo objective (Zeiss). For the PM-localized CESA6 FRAP, photobleaching was performed with a Vector scanner (Intelligent Imaging Innovations) with a 515-nm laser line at 100% power and 1 ms/scan. Time-lapse images were collected at the PM with a 10-s interval for 64 frames, with photobleaching in a small region (44.2 μm$^2$) after the 4th frame, and recovery for total 10 min.

SDCM Image Processing and Quantification

Image analysis was performed using ImageJ. For CESA particle density analyses, regions of interest (ROIs) without abundant Golgi signals were chosen using the Freehand selection tool. CESA particles were detected automatically on 8-bit images using the Find Maxima tool with the same noise threshold for all images. CESA particle density for each ROI was calculated by dividing the number of particles by the ROI area. To analyze CESA particle dynamics, 5-min time-lapse series with 5-s intervals were collected. Average intensity projections were generated to identify the trajectories of CSC particles. Image drift was corrected using the StackReg plugin (Thevenaz et al., 1998). Kymographs were generated, and the velocities of CESA particles were measured as the reciprocal of the slope of individual CESA particles in the kymographs. To quantify cortical vesicles, 1 μm z-series stack with 0.2 μm as the step size and 20-s time-lapses were collected. The focal plane at 0.4 μm below the PM was used for cortical SmaCC analysis. Small particles showing motility in time-lapse series were considered to be SmaCCs. For the FRAP assay of PM-localized CSCs, a smaller area (16 μm$^2$) within the bleached region was used for analyses. The CSC delivery events during the first 5 min of recovery were manually counted according to the criteria described previously (Li et al., Proc. Natl. Acad Sci. USA, 2016, 113, 11348-11353). The particles which exhibited steady linear movement at the PM were considered as new delivery events. The CSC delivery rate was calculated by dividing the number of delivery events by the measured area and time.

Homology Modeling and Molecular Docking Analysis

Homology modeling of full-length AtCESA6 structure was performed using SWISS-MODEL server (Waterhouse et al., Nucleic Acids Res. 2018, 46, W296-W303) with the structure of PttCESA8 (Protein Data Bank ID:6WLB) as a template. Based on the sequence alignment information of AtCESA6 and PttCESA8, and under the guidance of the three-dimensional structure of PttCESA8, the three-dimensional protein structure of AtCESA6 was generated online automatically. The SWISS-MODEL homology modeling report shows that the sequence of AtCESA6 shares 51% similarity with the PttCESA8. The GMQE score of the AtCESA6 modeling is 0.56 and the QMEAN Z-score is −3.48, which are both within acceptable ranges. The CSR domain of PttCESA8 is an unstructured region on cryo-EM structure and cannot be aligned with the CSR of AtCESA6 in modeled full-length AtCESA6. Molecular docking analysis of ES20, ES20-1 and other CBIs on modeled full-length AtCESA6 was performed using Autodock Vina of PyRx software (Trott and Olson, J. Comput Chem. 2010, 31, 455-461). The entire modeled full-length CESA6 structure was used to find the possible binding sites for different small molecules. Figures were prepared using PyMOL v.1.7.6.7 software.

Bacterial Cellulose Biofilm Production

Komagataeibacter xylinus (previously named Gluconacetobacter xylinus) ATCC strain 700178 was obtained from ATCC (Manassas, Va., USA) to evaluate cellulose production. HS (Hestrin and Schramm) medium was used for culture; HS liquid medium contains 2.0% glucose (w/v), 0.5% yeast extract (w/v), 0.5% peptone (w/v), 0.27% Na$_2$HPO$_4$ (w/v), and 0.15% citric acid (w/v), pH 5.0, and HS solid medium was solidified with 1.8% agar (w/v). To prepare the initial inoculation source, a single K. xylinus colony grown on HS solid medium was transferred to HS liquid medium and cultured at 26° C. for 5 days under static conditions. We used cells from the bottom of the liquid culture as the initial inoculation source to avoid biofilm aggregates at the air-liquid interface. To test the effect of ES20 and ES20-1 on the bacteria growth, initial inoculation source was series diluted and 20 μL culture from each diluted solution was dropped on HS solid medium supplemented with DMSO (0.1%) or different concentrations of ES20 and ES20-1 and cultured at 26° C. for 6 days after the dropped culture was completely dry. To test the effects of ES20 and ES20-1 on cellulose production, the prepared inoculation source was inoculated at a dilution ratio of 1:1000 dilution in HS liquid medium supplemented with 0.1% DMSO or 20 μM of ES20 or ES20-1. Static cultivation was carried out in a 26° C. incubator, and agitated cultivation was carried out at 26° C. with shaking at 220 rpm. To isolate cellulose from pellicles, the pellicles were removed from liquid culture, washed several times with deionized water, and soaked in 0.1 M NaOH at 80° C. for 2 h. The pellicles were washed several times with deionized water to completely remove the alkali. The purified cellulose was dried at 60° C. for ~1 day until a constant dry mass was reached.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected. It should be understood by those skilled in the art that various alternatives to the embodiments described herein may be employed in practicing the claims without departing from the spirit and scope as defined in the following claims.

What is claimed is:

1. A method of weed control for a field of a plant comprising the step of applying a cellulose biosynthesis inhibitor selected from the group consisting of

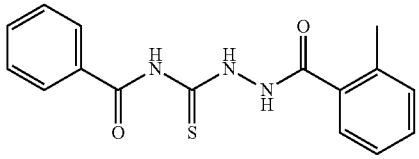 [SMILES: Cc1ccccc1C(=O)NNC(=S)NC(=O)c1ccccc1]

or a salt thereof, in combination with isoxaben, together with one or more diluents, to a field in need of said weed control.

2. The method of claim 1, wherein said cellulose biosynthesis inhibitor and other herbicides are applied to a field of a plant together as a mixture of preformulated single product.

3. The method of claim 1, wherein said cellulose biosynthesis inhibitor and other herbicides are applied to a field of a plant separately as an individually pre-formulated product, consequentially or concurrently.

4. The method of claim 1, wherein said plant is resistant to said cellulose biosynthesis inhibitor

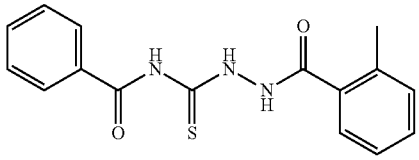 [SMILES: Cc1ccccc1C(=O)NNC(=S)NC(=O)c1ccccc1]

or a salt thereof.

5. The method of claim 1, wherein said plant is a crop for food or feed.

* * * * *